(12) United States Patent
Kalinowski et al.

(10) Patent No.: US 7,591,779 B2
(45) Date of Patent: Sep. 22, 2009

(54) ADAPTATION RESISTANT ANTI-STUTTERING DEVICES AND RELATED METHODS

(75) Inventors: Joseph Kalinowski, Greenville, NC (US); Andrew M. Stuart, Winterville, NC (US); Vijaya Guntupalli, Greenville, NC (US); Tim Saltuklaroglu, Knoxville, TN (US)

(73) Assignee: East Carolina University, Greenville, NC (US)

( * ) Notice: Subject to any disclaimer, the term of this patent is extended or adjusted under 35 U.S.C. 154(b) by 652 days.

(21) Appl. No.: 11/213,581

(22) Filed: Aug. 26, 2005

(65) Prior Publication Data

US 2007/0049788 A1    Mar. 1, 2007

(51) Int. Cl.
  *A61F 5/58* (2006.01)
(52) U.S. Cl. .................................. 600/23; 434/185
(58) Field of Classification Search .......... 600/23–24, 600/300; 128/905, 897; 704/271; 434/185
  See application file for complete search history.

(56) References Cited

U.S. PATENT DOCUMENTS

| 4,464,119 A | 8/1984 | Vildgrube et al. ........... 434/185 |
| 4,662,847 A | 5/1987 | Blum |
| 4,727,582 A | 2/1988 | de Vries et al. ............ 381/330 |
| 5,133,016 A | 7/1992 | Clark .......................... 381/28 |
| 5,659,156 A | 8/1997 | Mauney et al. .............. 181/130 |
| 5,765,134 A | 6/1998 | Kehoe ......................... 704/270 |
| 5,812,659 A | 9/1998 | Mauney et al. .............. 379/430 |
| 5,961,443 A | 10/1999 | Rastatter et al. ............... 600/23 |
| D469,081 S | 1/2003 | Perszyk et al. ............. D14/205 |
| 2006/0122826 A1 | 6/2006 | Jiang et al. |

FOREIGN PATENT DOCUMENTS

| WO | WO0224126 | 3/2002 |
| WO | WO03091988 | 6/2003 |
| WO | WO2004032816 | 4/2004 |

OTHER PUBLICATIONS

Curio et al., *Speaking Modifies voice-Evoked Activity in the Human Auditory Cortex*, 2000 Wiley-Liss, Inc., Human Brain Mapping 9:183-191(2000).
Smotherman, M., *Sensory feedback control of mammalian vocalizations*, 2007 Elsevier B.V.; Behavioural Brain Research 182 (2007):315-326.
International Search Report and the Written Opinion, dated Jan. 19, 2007 for corresponding PCT application No. PCT/US2006/031920 (17 pages).
International Search Report and the Invitation to Pay Additional Fees, dated Dec. 8, 2006 for corresponding PCT application No. PCT/US2006/031920 (8 pages).
Fox et al., *Stuttering more than talk-research shows brain's role in disorder*, Purdue News, Jul. 22, 2004.

(Continued)

*Primary Examiner*—John P Lacyk
(74) *Attorney, Agent, or Firm*—Myers, Bigel, Sibley & Sajovec, P.A.

(57) ABSTRACT

Portable devices for treating stuttering or communication disorders include a circuit configured to automatically electronically select sua sponte different signal parameters and/or sound effect algorithms used to generate varied altered auditory feedback signals to a user over time.

73 Claims, 21 Drawing Sheets

OTHER PUBLICATIONS

Kalinowski et al., *A Common Element In The Immediate Inducement Of Effortless, Natural-Sounding, Fluent Speech In People Who Stutter: 'The Second Speech Signal'*, Medical Hypotheses 58(1), pp. 61-66, 2002.

Kalinowski et al., *Effects of Alterations in Auditory Feedback and Speech Rate on Stuttering Frequency*, Language and Speech 36(1), p. 1-16, 1993.

Kalinowski et al., *Gestural recovery and the role of forward and reversed syllabic repetitions as stuttering inhibitors in adults*, Neuroscience Letters 363, pp. 144-149, 2004.

Smith, D., *Signals, Samples and Stuff: A DSP Tutorial (Part 1)*, pp. 3-16, Mar./Apr. 1998.

Stuart et al., *Self-Contained In-The Ear Device to Deliver Altered Auditory Feedback: Applications for Stuttering*, Annals of Biomedical Engr. vol. 31, pp. 233-237 (2003).

http://users.iafrica.com/k/ku/kurient/dsp/algorithms.html, Audio Effect Algorithms, 10 sheets, Date unknown but believed to be before Aug. 2005.

*Studio 400 4 in-4 out Professional Studio Effects Processor*, DigiTech, pp. 1-44, Copyright 1996.

*DSP 16 Effects Processor*, DigiTech, 49 pages, Copyright 1991.

ITE
Full Shell

HS
Half Shell

ITC
Canal

MC
Mini Canal

CIC
Completely in Canal

ADAPTATION RESISTANT ANTI-STUTTERING DEVICES AND RELATED METHODS

FIELD OF THE INVENTION

The present invention relates to treatments for stuttering and/or other communication disorders.

BACKGROUND OF THE INVENTION

Recently, a small portable in-the-ear ("ITE") device known as the SpeechEasy™ has been used to treat stuttering using a digital signal processor to generate delayed auditory feedback ("DAF") and/or frequency altered feedback ("FAF"). See also, U.S. Pat. No. 5,961,443.

However, chronic use of the device in some users can result in the signal becoming less effective over time as some users may adapt to the altered auditory feedback ("AAF") input. To address this issue, some users have returned to a clinic to have signal parameters adjusted periodically (e.g., monthly), to address the reported adaptation to the altered feedback (DAF and/or FAF) signal generated by the device.

SUMMARY OF EMBODIMENTS OF THE INVENTION

The present invention is directed to adaptation resistant devices, methods and computer program products that automatically electronically vary one or more parameters associated with an altered auditory feedback signal.

In some embodiments, the sound effect(s) used to generate the AAF signal to a user can be changed over time and its duration or duty cycle can also change. In other embodiments, the same AAF can be used but with different delays, shifts, durations or duty cycles. The devices may be configured to change any one or more parameters associated with signal processing at any time and for any duration.

The present invention may be particularly suitable for treating stuttering, but may also be used for non-stuttering pathologies, particularly communication-based disorders, using altered auditory feedback.

Some embodiments are directed to portable devices for treating stuttering or communication disorders. The portable devices include a circuit configured to automatically electronically change sua sponte one or more parameters used to generate an altered auditory feedback to a user over time.

The one or more parameters can be associated with different sound effect algorithms used to generate varied altered auditory feedback signals to a user over time.

The circuit may include a digital signal processor, a receiver in communication with the digital signal processor, the receiver configured to generate an input signal responsive to an auditory signal associated with a user's speech. The circuit may also include an altered auditory feedback circuit including a sound effect selector module operably associated with the receiver and the digital signal processor for generating and transmitting the altered auditory signal to the user.

The circuit may be configured to intermittently employ the sua sponte selected at least one sound effect algorithm for a short duration to generate the altered auditory feedback signal and primarily output at least one of an FAF or DAF altered auditory feedback signal at other times.

Other embodiments are directed to methods for treating stuttering or communication disorders. The methods include: (a) receiving a speech signal from a user; (b) selecting sua sponte, at least one of a plurality of programmatically selectable parameters, signal effects and sound effects; then (c) digitally generating an altered auditory feedback signal using the received speech signal and the sua sponte selected parameter and/or effect to thereby provide an adaptation resistant altered feedback signal to the subject.

The sua sponte selected at least one sound effect may be configured to stimulate or influence the neuro-acoustic activity of a user by interrupting the hearing using a relatively disruptive feedback signal that is activated intermittently over time for a short duration intermixed with a standard altered auditory feedback operating mode (using conventional relatively acoustically transparent FAF and/or DAF altered auditory feedback signals).

In some embodiments, the selecting is carried out in a pseudo-random manner. In some particular embodiments, the programmatically selectable sound effects have an identifier or memory location, and selecting is carried out by serially selecting the programmatically selectable sound effects.

In certain embodiments, the devices and methods can be devised to provide the adaptation resistant input using a miniaturized, minimally obtrusive device that can be worn so as to promote chronic use or therapy (upon demand where and when needed) and the like. The device may be configured to include an ear-mounted member that wirelessly communicates with a second (pocket) member. In other embodiments, the device can be a self-contained device. In each case, the device may include an ear mounted housing that can be sized and/or shaped as one of a behind-the-ear ("BTE"), an in-the-ear ("ITE"), in-the-canal ("ITC"), or completely-in-the-canal ("CIC") device.

In certain embodiments, the device is configured to allow treatment by ongoing substantially "on-demand" use while in position on the subject separate from and/or in addition to clinically provided episodic treatments during desired periods of service.

In particular embodiments, the signal processor is a digital programmable signal processor having sua sponte programmably selectable and/or adjustable signal parameters.

Still other embodiments are directed to computer program product for generating an adaptation resistant altered auditory feedback signal to a patient. The computer program product includes a computer readable storage medium having computer readable program code embodied in the medium. The computer-readable program code includes: (a) computer readable program code configured to define a plurality of different sound effects, each associated with a unique identifier; (b) computer readable program code configured to automatically select at least one of the plurality of different sound effects for use in generating an altered auditory feedback signal intermittently for a short duration; and (c) computer readable program code configured to generate an altered auditory feedback signal using a speech signal from the patient and the selected at least one sound effect to thereby provide an adaptation resistant altered feedback signal to the patient.

These and other objects and/or aspects of the present invention are explained in detail in the specification set forth below.

DETAILED DESCRIPTION OF EMBODIMENTS OF THE INVENTION

Figure 1:
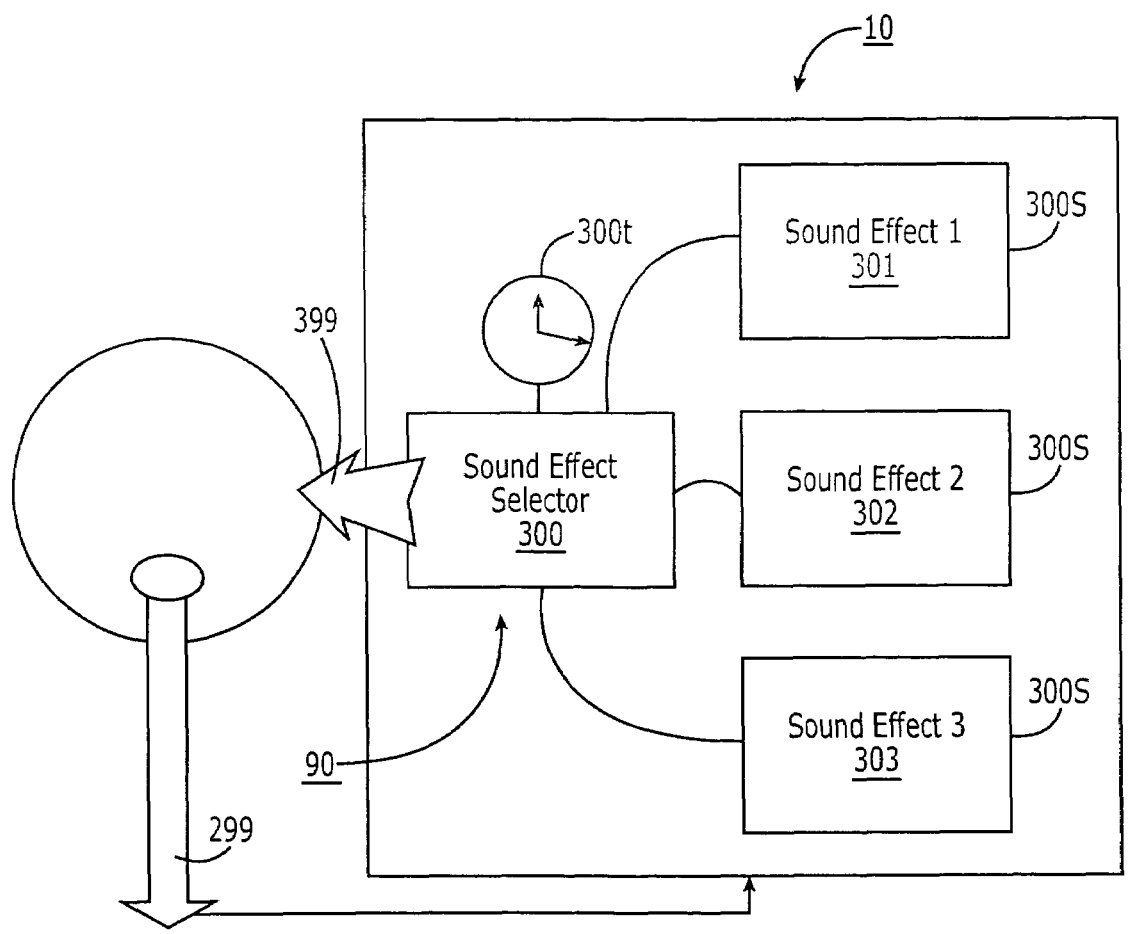
FIG. 1 is a schematic diagram of an altered auditory feedback system according to embodiments of the present invention.

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

In the description of the present invention that follows, certain terms are employed to refer to the positional relationship of certain structures relative to other structures. As used herein, the term "distal" and derivatives thereof refer to a direction extending away from the ear canal (away from the center of the skull), while the term "proximal" and derivatives thereof refer to a location in the direction of the ear canal extending toward the center of the skull.

Generally described, the present invention is directed to methods, systems, and therapeutic devices for treating subjects. The invention may be particularly suitable for treating stuttering. However, it is contemplated that the devices and methods may also be used to treat subjects having non-stuttering pathologies to facilitate and/or improve communication skills, including reading ability and/or writing, spelling, and the like. The term "communication skills" includes, but is not limited to, writing, speech, and reading. The term "writing" is used broadly to designate assembling symbols, letters and/or words to express a thought, answer, question, or opinion and/or to generate an original or copy of a work of authorship, in a communication medium (a tangible medium of expression) whether by scribing, in print or cursive, onto a desired medium such as paper, or by writing via electronic input using a keyboard, mouse, touch screen, or voice recognition software. The term "reading ability" means reading comprehension, cognizance, and/or speed.

The term "sua sponte" means of its own will; that is, selection and/or activation of an altered auditory feedback, sound effect and/or audio acoustic parameter used to generate the altered auditory feedback to a user is electronically changed by the device itself rather than by a user and changed over time. Thus, rather than using the same signal effect (such as a FAF/DAF feedback signal which is typically relatively acoustically transparent) over a treatment period, or forcing a user to manually change the signal (or visit a clinician), the device is configured to automatically change the signal effect used so that the user will hear different altered auditory feedback signals at different times during operation, without controlling and/or knowing when the change will occur, to thereby inhibit the mental adaptation to the same altered auditory feedback signal that can occur over time. As such, the user can expect the unexpected. The signal effect used to generate an altered auditory signal may be a relatively powerful effect that does not emulate normal hearing, is not acoustically invisible and alters one or more of pitch, tone and speed, so as to be able to influence the psychoacoustic signal of a user, at least intermittently over a user period, to thereby increase fluency in stutterers.

In some embodiments, the sound effect used to generate one or more of the AAF signals contemplated by the instant invention may interfere with speech intelligibility in the aided ear, but the other ear may compensate for this effect with the end result promoting increased fluency.

The devices can be configured to change or employ a signal effect at certain (constant or irregular) intermittent time intervals. The intermittent timing can be carried out so that at least one changed or different signal effect is used to generate the altered auditory feedback to a user between about every 1-8 hours during at least one day in an operative weekly period.

In some embodiments, the signal effect or signal parameter change can be made about every 1-60 minutes (although some embodiments contemplating changing the signal in under 1 minute at least some of the time), every 1-24 hours, daily or multiple times a day, or weekly. The time of change and duration of the signal effect or parameter change can vary.

For example, one or more of the signals can have a duration of about 1 second to about 1 day or even longer. Another signal may have the same or a different duration. Some non-consecutive signals can have a relatively brief period of about 5 seconds or less, but typically between about 30 seconds to about 15 minutes during an hourly, daily or weekly operating interval.

A signal effect or sound effect signal may have increasing or decreasing durations at different points in time, or may have a relatively constant duration. It is currently believed that the signal should change at least once for at least a short time frame (such as between about one second to about thirty minutes) at least about every three days, and likely several times a day, to inhibit adaptation. The time intervals at which a different sound effect can be used and/or the length of time that it is used can automatically vary so that a user will not know (or easily predict) when the change will occur.

In some embodiments, the change in the signal effect, typically the sound effect, used to generate the altered auditory feedback can alternatively or additionally occur upon detection of a stuttering event and/or detection of an increase in stuttering events over a certain time period, such as from between about 10-60 minutes to between about 1-8 hours, and the like.

The sound effects can be programmed into a memory array of effects. The sound effects stored into memory can be customized based on a user's response to test signals during a "fitting" session by a clinician. Some user devices may employ between about 3-10 different signal and/or sound effects, others may employ between 10-50, and still others may employ between about 50-100.

The term "automatically" means that the operation can be electronically and/or programmatically directed and carried out without requiring manual input. The term "programmatically" means under the direction of computer, processor or circuit implemented instructions. The term "circuit" refers to embodiments combining software and/or hardware aspects, and may also be generally referred to herein as a "module." The term "continuously" means that the sound effect used to generate the altered auditory feedback is automatically changed over time at irregular or regular intervals (which may occur during operation of the device). The term "algorithm" describes computer or processor implemented instructions (digital code) that generate a desired sound effect, typically using a circuit with a digital signal processor.

The term "pseudo-random" means that the sound effect is a computer-generated random selection. The prefix pseudo- is used to distinguish this type of operation from a "truly" random selection occurrence generated by a random physical process such as radioactive decay. Thus, to a user, the sound effect is generated in what appears to be a random format but is selected by the device and may be temporally selected "on-line" by the device. A discussion of pseudo-random algorithms can be found at URL (http://)en.wikinedia.org/wiki/Pseudorandom_number_generator.

The pseudo-random operation can employ a single or multi-parameter computer algorithm that automatically selects a time of change, a type or signal effect, a change in a signal effect, and/or duration of altered signal output to generate pseudo-random patterns of alteration to influence the brain into new neural organization so that adaptation may be less likely. The pseudo-random operation may be carried out using a defined mathematical selection model or a random number generator model with each sound effect having a corresponding assigned number.

In some embodiments, the signal change can be carried out to generally maintain a desired or original stuttering inhibition set-point or result that is achieved when the anti-stuttering device is initially employed with a first altered auditory signal type. Over time, the device can automatically change the altered auditory output. Previously used signals may be reused (as there is still potency after a period of non-use of a prior signal) and new signals may also be used. A new signal may employ a used signal with a varied parameter (pitch delay or the like). It is also noted that the signal change can be carried out in a non-random manner as well as a pseudo-random manner (i.e., by serially stepping through the sound effects).

The term "sound effect" refers to one or a set of operational parameters that generate user detectable audio and/or acoustic sounds. Sound effects generated by digital signal processors and their associated parameters are well known to those of skill in the art. The sound effects can be generated using digital and/or hardware filters, signal manipulation, mixing, modulation, delays, transformation, phase shifters, exciters, complex carriers, receivers and other signal processing modules or circuits. See, e.g., Doug Smith, *Signals, Samples and Stuff: A DSP Tutorial (Part* 1), QEX, pp. 1-16, March/April 1998, the contents of which are hereby incorporated by reference as if recited in full herein. The term "signal effect" refers to one or more of the parameters used to generate a respective altered auditory feedback signal and may be, but is not required to be, associated with a particular sound effect (see, e.g., Table I for an exemplary list of parameters that have adjustable default settings). That is, for a change in signal effect, the same "sound effect" may be generated but at least one of the parameters is different. For example, a delay parameter can be changed to generate a shorter or longer DAF signal.

The term "sound effect selector" refers to a circuit or module used to determine when to change the sound or signal effect used to generate the altered auditory feedback and/or which one or more of a signal effect, sound effect and/or associated audio and acoustic parameters to employ or change.

Examples of some sound effects include, but are not limited to: reverberation, environmental (shower, hall, cave, roadway, airport, stadium, carnival, etc), chorus, panning, echoes, fades, and the like, each of which can be used in different manners to generate different sound effects (alone or in combination) by using different operational parameters, such as associated time delays, modulation, frequency shift, filters, amplitude, bandwidth, and the like. See, e.g., Digitech® at digitech.com, a manufacturer having a location in Amherst, N.H., that provides vocal effects processors such as the DSP 16 or DSP 128. The first has an owner's manual that describes 16 different digital reverb and delay effects describes and the second describes 128 different "preset" programs having program numbers P1-P128. Examples of different parameters associated with one or more sound effect program or algorithm include the following, with examples of ranges for each stated in parenthesis: Accent amplitude (reverse reverb effects with a range of 0-10), delay time or multi-tap; right, delay range (can be broken down into ranges 1-4 associated with different time delays such as 0-249 ms, 250-440, etc), delay level (for a relative strength of delay from 0-10), feedback (delay, the amount of the e signal that is internally fed back in the delay (range 0-99), delay time, multi-tap, left delay (range 0.000-1.8), center, delay time, multi-tap center delay and multi-tap feedback delay (both with range of 0.000-1.8), low pass filter frequency cut-off frequency (the high frequency roll off point for the low pass filter—range 0.40-12), animation velocity for chorus and flange effects affecting velocity at which the delay tap is swept (0-99), animation distance for chorus and flange effects (distance through which delay tap is swept thereby adjusting the depth of chorus or flange effect—range 0-99), chorus delay (0-60), chorus level (relative internal level of chorus effect—0-10), flange delay time (initial amount of time delay in flange effect—0-10), flange feedback (amount of signal that is internally feedback in flange delay, 0-99), flange level (relative internal level of flange effect, 0-10), initial reflections (reverb effects, relative stretch of the first echoes for a subjective positioning effect of the listener front to back in filed, softer, the further back—0-10, such as for a 1-6 m Hall), bounce texture (apparent hardness or softness to the rebound bounce of the sound—0-4), stereo image (subjective width of stereo image 1-6), and MIDI channel number (channel number available for reception and transmission of data, 0 bits is off, can use up to 16 bits in a 16 bit signal processor, and up to 32 bits in a 32 bit processor).

The system can alternatively or additionally generate broadband white or pink noise and/or narrow band components of white or pink noise (more commonly known as masked auditory feedback "MAF") to provide one or more of the AAF signal(s). For a discussion of masking, see, e.g., Kalinowski, J., Armson, J., Roland-Mieszkowski, M., Stuart, A., & Gracco, V. (1993). *The effects of alterations in auditory feedback on stuttering frequency*. Language and Speech, 36, 1-16.

Unlike conventional AAF signals (MAF can be considered one type of AAF), the adjustable signal parameters need not be limited to just frequency shifts or delays or masking of the user's speech and may be designed to temporally substantially alter the user's speech in a relatively dramatic audio/acoustic manner to mentally stimulate and/or inhibit adaptation and increase treatment efficacy. However, it is contemplated that the device may also be configured to use any suitable signal effect that is perceptually significant to the person that stutters. For example, it may be sufficient to sua sponte alter the signal by a delay that is increased or decreased sufficiently, such as at least about +/−30 ms for some stutterers.

The devices of the instant invention may be configured to change any operational parameter at any (operational) time for any duration to provide the sua sponte changed altered auditory feedback. For example, one AAF signal can include a 50 ms delay and another AAF can include a 100 ms delay. Which signal effect is used, the duration and/or duty cycle of each type of signal effect can be programmatically selected. In some embodiments, the selection of the type of signal, as well as the duration (any time) and duty cycle (0-100%, typically 10-100&) or when the signal is used can be made sua sponte by the device. Thus, a 50 ms DAF signal can be used for a 50% duty cycle for a 24 hour time period. So, for a 50% duty cycle, the signal can have different selectable or adjustable formats, such as: 12 hours on, 12 hours off, 1 hour on, 1 hour off, 1 minute on, 1 minute off or any other desired activation/output format.

The sound effect selector can comprise two operational modes, a primary operating mode employing a conventional AAF signal and a secondary operating mode that intermittently provides a sound-effect altered auditory signal (which may be changed over time). The timing of each mode to activate the associated signal can be electronically automatically selected. In some embodiments, each, or only one of the types of primary or secondary signals may also be automatically electronically changed over time.

In some particular embodiments, in contrast to an acoustically transparent AAF signal, a sound effect based altered auditory signal can be activated and transmitted intermittently for a relatively brief period.

The primary mode may be activated using a bypass or off mode whereby a conventional AAF signal may also be output by the device or by using a defined primary operational mode. Indeed, some particular devices contemplated by the instant invention may be generally primarily configured to output conventional AAF signal(s) which is relatively acoustically transparent so as to not unduly impede hearing in the aided ear and uses a more dominant sound effect altered auditory feedback signal(s) intermittently.

The devices contemplated by the instant invention may use MIDI (Musical Instrument Digital Interface) standardized interface protocol to allow for electronic download of established sound effects. This MIDI protocol has defined codes to represent volume dynamics, notes on and off, pitch bend, patch change and the like. In other embodiments, customized protocols may be used. Exemplary sound effect algorithms and parameters and ranges as defined by a DIGITECH product are provided in the below chart.

TABLE I

EXEMPLARY EFECTS AND PARAMETERS

| Effect Description | Parameters | Ranges |
| --- | --- | --- |
| Bounce Effect, Filter | Low Pass Filter | 400 Hz-12 kHz |
|  | Decay Time | 0.6-2.0 sec. |
|  | Bounce Texture | 0-4 |
| Chorus, Delay, Filter | Low Pass Filter | 400 Hz-12 kHz |
|  | Animation Velocity | 0-99 |
|  | Animation Distance | 0-99 |
|  | Chorus Delay Time | 0-60 msec. |
|  | Chorus Level | 0-10 |
|  | Delay range | 1-5 |
|  | Delay time | 0-1.8 sec. |
|  | Delay Feedback | 0-99% |
|  | Delay Level | 0-10 |
| Delay, Filter | Low Pass Filter | 400 Hz-12 kHz |
|  | Delay Range | 1-5 |

TABLE I-continued

EXEMPLARY EFECTS AND PARAMETERS

| Effect Description | Parameters | Ranges |
| --- | --- | --- |
|  | Delay Time | 0-1.8 sec. |
|  | Delay Feedback | 0-99% |
| Flange, Delay, Filter | Low Pass Filter | 400 Hz-12 kHz |
|  | Animation Velocity | 0-99 |
|  | Animation Distance | 0-99 |
|  | Chorus Delay Time | 0-60 msec. |
|  | Chorus Level | 0-10 |
|  | Delay Range | 1-5 |
|  | Delay Time | 0-1.8 sec. |
|  | Delay Feedback | 0-99% |
|  | Delay Level | 0-10 |
| Gated Reverb, Filter | Low Pass Filter | 400 Hz-12 kHz |
|  | Pre-Delay | 0-90 msec. |
|  | Decay Time | 50-600 msec. |
| Hall Reverberation, Filter | Low Pass Filter | 400 Hz-12 kHz |
|  | Pre-Delay | 0-90 msec. |
|  | Initial Reflection Level | 1-6 |
|  | Decay Time | 0.1-30 sec. |
| Large Room, Delay, Chorus | Pre-Delay | 0-90 msec. |
|  | Decay Time | 1.0-20 sec. |
|  | Reverb Level | 0-10 |
|  | Delay Range | 1-4 |
|  | Delay Time | 0-999 msec. |
|  | Delay Feedback | 0-99% |
|  | Delay Level | 0-10 |
|  | Animation Velocity | 0-99 |
|  | Animation Distance | 0-99 |
|  | Chorus Delay Time | 0-60 msec. |
|  | Chorus Level | 0-10 |
| Large Room, Delay, Filter | Low Pass Filter | 400 Hz-12 kHz |
|  | Pre-Delay | 0-90 msec. |
|  | Initial Reflection Level | 0-10 |
|  | Decay Time | 100-1000 msec. |
|  | Reverb Level | 0-10 |
|  | Delay Range | 1-4 |
|  | Delay Time | 0-999 msec. |
|  | Delay Feedback | 0-99% |
|  | Delay Level | 0-10 |
| Live Large Room, Filter | Low Pass Filter | 400 Hz-12 kHz |
|  | Pre-Delay | 0-90 msec. |
|  | Decay Time | 1.0-20 sec. |
| Live Medium Room, Filter | Low Pass Filter | 400 Hz-12 kHz |
|  | Pre-Delay | 0-90 msec. |
|  | Decay Time | 0.4-4.0 sec. |
| Medium Room, Delay, Chorus | Pre-Delay | 0-90 msec. |
|  | Decay Time | 0.3-2.8 sec. |
|  | Reverb Level | 0-10 |
|  | Delay Range | 1-4 |
|  | Delay Time | 0-999 msec. |
|  | Delay Feedback | 0-99% |
|  | Delay Level | 0-10 |
|  | Animation Velocity | 0-99 |
|  | Animation Distance | 0-99 |
|  | Chorus Delay time | 0-60 msec. |
|  | Chorus Level | 0-10 |
| Medium Room, Delay, Filter | Low Pass Filter | 400 Hz-12 kHz |
|  | Pre-Delay | 0-90 msec. |
|  | Initial Reflection Level | 0-10 |
|  | Decay Time | 100-1000 msec. |
|  | Reverb Level | 0-10 |
|  | Delay Range | 1-4 |
|  | Delay Time | 0-999 msec. |
|  | Delay Feedback | 0-99% |
|  | Delay Level | 0-10 |

TABLE I-continued

EXEMPLARY EFECTS AND PARAMETERS

| Effect Description | Parameters | Ranges |
|---|---|---|
| Multi-tap Delay, Filter | Low Pass Filter | 400 Hz-12 kHz |
| | Left Delay Time | 0-1.8 sec. |
| | Middle Delay Time | 0-1.8 sec. |
| | Right Delay Time | 0-1.8 sec. |
| | Feedback Delay Time | 0-1.8 sec. |
| | Delay Feedback | 0-99% |
| Multi-Tap Delay, Reverse Reverb, Filter | Low Pass Filter | 400 Hz-12 kHz |
| | Left Delay Time | 0-1.8 sec. |
| | Middle Delay Time | 0-1.8 sec. |
| | Right Delay Time | 0-1.8 sec. |
| | Feedback Delay Time | 0-1.8 sec. |
| | Delay Feedback | 0-99% |
| | Decay Time | 100-600 msec. |
| Mute | None | Not Applicable |
| Reverse Reverb, Filter | Low Pass Filter | 400 Hz-12 kHz |
| | Decay Time | 100-600 msec. |
| | Accent Amplitude | 0-10 |
| | Accent Envelope | −50-+50 msec. |
| Small Room, Delay, Filter | Low Pass Filter | 400 Hz-12 kHz |
| | Pre-Delay | 0-90 msec. |
| | Initial Reflection Level | 0-10 |
| | Decay Time | 100-1000 msec. |
| | Reverb Level | 0-10 |
| | Delay Range | 1-4 |
| | Delay Time | 0-999 msec. |
| | Delay Feedback | 0-99% |
| | Delay Level | 0-10 |
| Stereo Image Generator, Filter | Low Pass Filter | 400 Hz-12 kHz |
| | Stereo Image | 1-6 |

Each of the sound effects includes several associated operational parameters and ranges. One or more of each of the parameters default settings can be electronically adjusted, typically by an OEM or fitter (i.e., set to a different value, set to "0" and the like). The primary mode of the device can operate using any suitable AAF, whether conventional or using sound effect programs or variations of same.

Turning now to the figures, referring to FIG. 1, when a user speaks, his or her speech 299 is detected by and input into a treatment device 10. The device 10 includes a circuit 90 with a sound effect selector 300 that can determine whether to apply a first sound effect 301 at a first time T1, a second sound effect 302 at the time T1 (or at another time T2, T3) and a third sound effect 303 at the time T1, or at a subsequent time (T2 or T3). The set of selectable sound effect signals can be identified by element number 300S. The sound effect selector 300 can be in communication with or include a timer and/or clock 300t that allows the sound effect selector to time the duration and/or select the activation time of a sound effect. The sound effect selector 300 can thus intermittently output the signal and/or sound effect for a relatively short period of time according to some particular embodiments of the present invention. The altered auditory feedback signal 399 generated using the selected sound effect and the user's speech 299 is transmitted to the user. Although shown as only three different selectable sound effects 301-303, more sound effects and/or selectable parameters may be used.

The sound effect selector 300 may be based on a random number generator, or may step through in a desired order (even, odd), serially (incrementally or decrementally) or other pattern to select the sound effect used. Each sound effect may be electronically stored in a block or array (such as a known column and/or row) of electronic media and/or may have a unique digital identifier (alphanumeric, numeric, etc.) that can be used to select (activate) a respective sound effect. The sound effect selector 300 can be configured to change the selected sound effect randomly (in time and/or the sound effect) or in a pseudo-random manner. For the random change, a random number generator can be used to select the program stored at that number or having that identifier. The change can be at constant time intervals or at different time intervals ranging in minutes to hours and days. The change can be carried out so that successive changes are at different time intervals.

In some embodiments, the device 10 is configured to change the sound effects used to generate the altered auditory feedback signal at different successive time intervals ranging from every minute to at least weekly. In some embodiments, the device 10 may be configured to change the sound effect used to generate the altered auditory feedback signal at least about 5 times per week, and typically at least about 20 times per week. The change in the signal effect can be at least once every other day to more frequently. For example, the device may change the signal at least about 3 times per day at different or constant successive time intervals and/or for a duration that is different or the same.

In particular embodiments, the device 10 is configured to change the signal and/or sound effect used to generate the altered auditory feedback signal at least 3 times per day at the same time interval at a different or the same duration while in others the change is carried out at least 3 times per day at different time intervals at a different or the same duration.

In some embodiments, the device 10 is configured to change the sound effect used to generate the altered auditory feedback signal at least once during a speaking cycle lasting more than about 5 minutes.

In some embodiments, the device 10 can output a signal or sound effect based altered auditory signal when a user starts to speak for a relatively short period, such as less than about 1 minute, then switch to a different AAF signal.

Figure 12A:
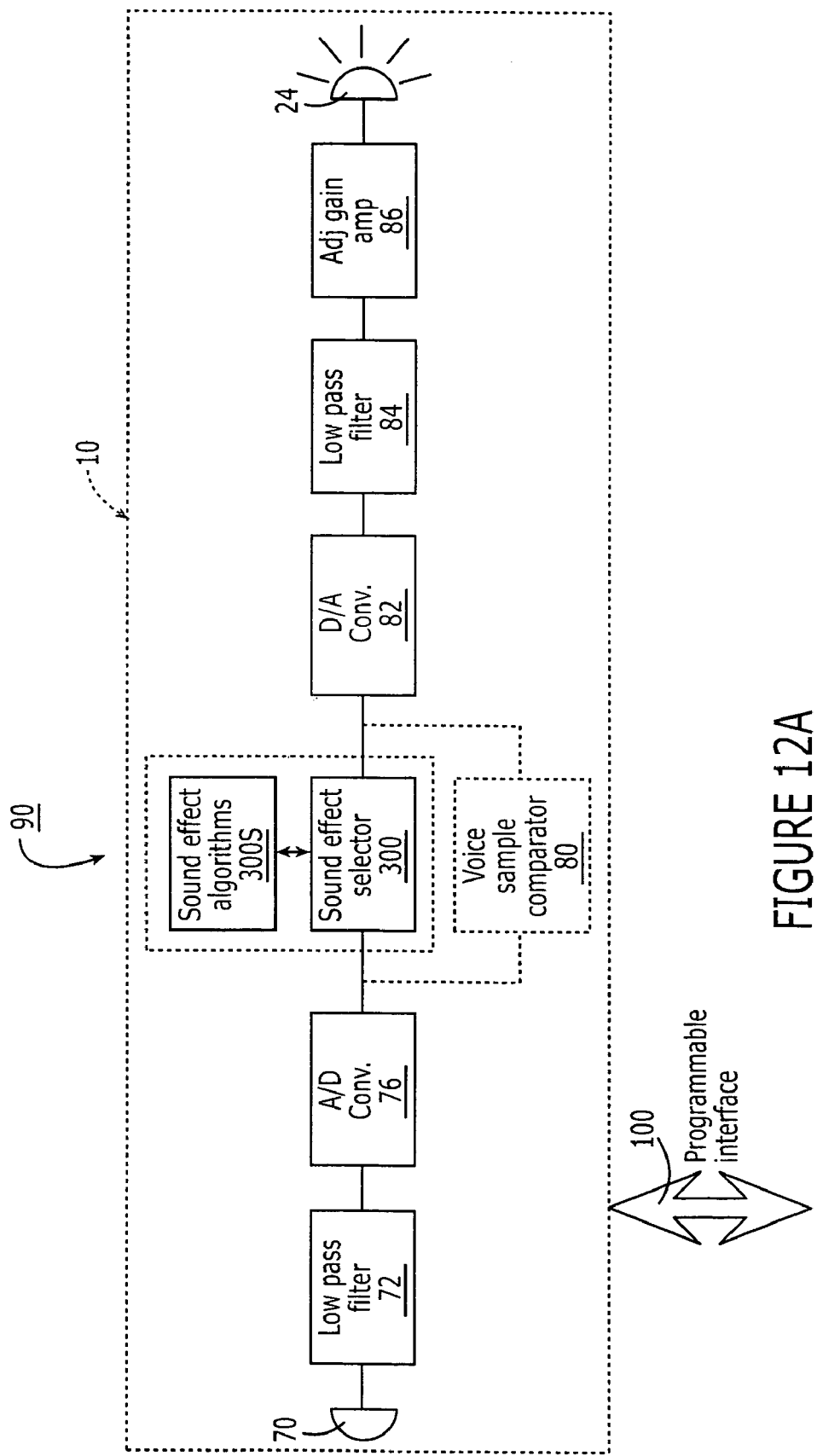
FIG. 12A is a schematic diagram of an exemplary signal processing circuit according to embodiments of the present invention.
Figure 12B:
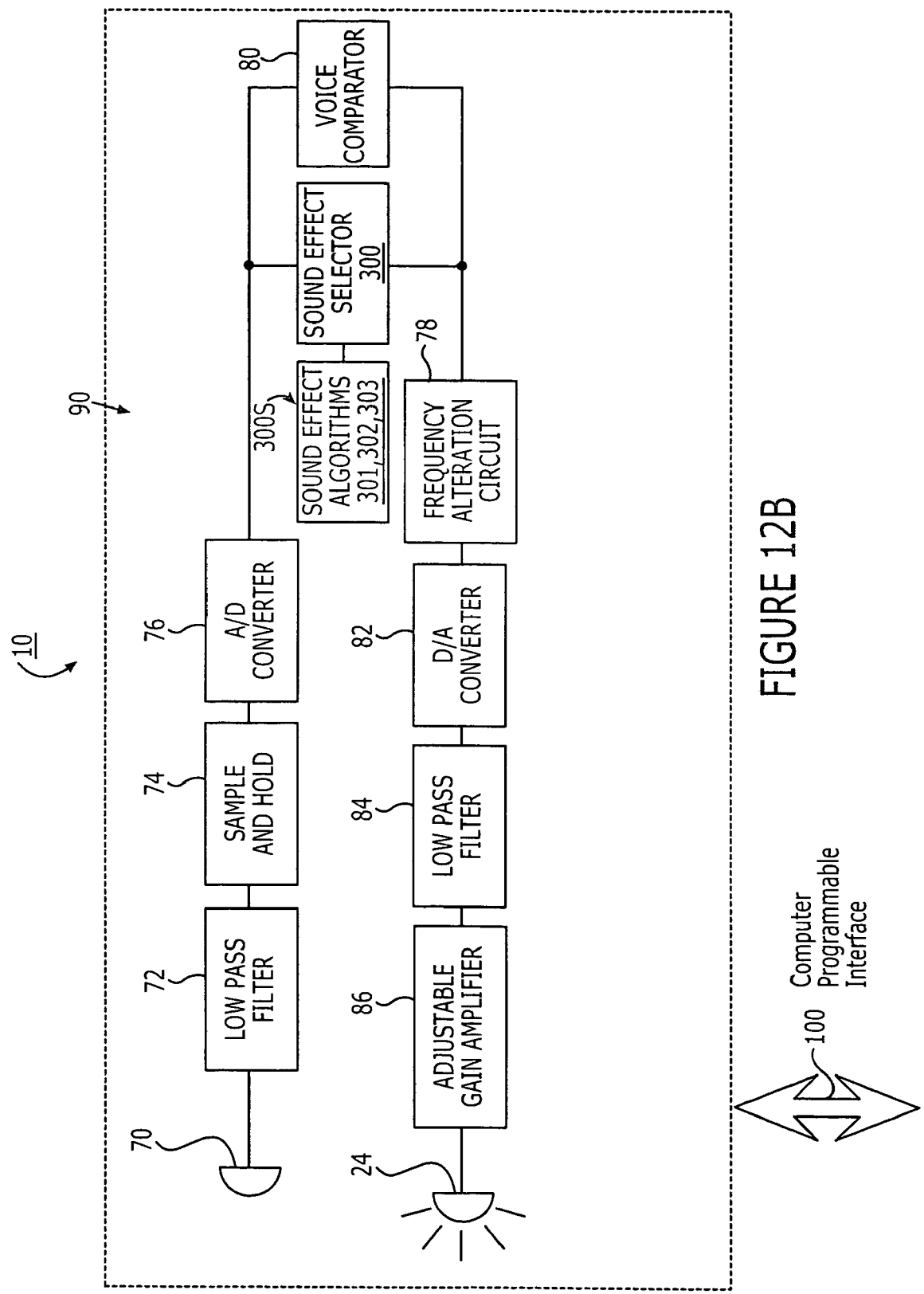
FIG. 12B is a schematic diagram of another exemplary signal processing circuit according to embodiments of the present invention.

As noted above, the device 10 can be configured to detect the onset of a stuttering event or an increase in the number of stuttering events (which can be done, for example, using a voice comparator 80 such as that shown in FIGS. 12A and 12B). The device 10 and/or selector 300 can be configured to change the sound effect used to generate the altered auditory feedback signal at least one in response to detection of a stuttering event.

In some embodiments, the device 10 can be configured to change the signal and/or sound effect used to generate the altered auditory feedback signal a plurality of times over an eight-hour operative time period relative to detection of a stuttering event and/or an increase in number of stuttering events. For example, the device 10 can be configured to successively change the sound effect used to generate the altered auditory feedback signal a plurality of times proximate in time to detection of a stuttering event.

As noted above, the device 10 may be configured to output the altered auditory feedback signal using at least one of a DAF, FAF or MAF signal intermittently with the sound effect signals. The device 10 can be configured to change the selected sound effect used to generate altered auditory signals intermittently and substantially continuously over use.

In some embodiments, the device 10 comprises computer readable media with computer program code defining at least 5 different programmatically selectable sound effects, each having predefined audio and/or acoustic sound generating parameters and a respective unique identifier.

The altered auditory feedback signal 399 is delivered to a subject having stuttering impediment or a non-stuttering pathology (disease, disorder or condition) that may subject him or her to impaired communication skills relative to individuals that are not afflicted with that pathology, proximate in time to when the subject is talking or speaking. The terms "talking" and "speaking" are used interchangeably herein and includes verbal expressions of voice, whether talking, speaking, whispering, singing, yelling, or otherwise audibly verbally outputting sound and whether to others or oneself. The pathology may present with a reading impairment.

In any event, the verbal output of a user should be sufficiently loud so that the auditory signal from the speaker's voice or speech can be detected by the device (which may be miniaturized as will be discussed below), whether the verbal output of the subject is associated with general talking, speaking, or communicating, or such talking or speaking is in relationship to spelling, reading (intermittent or choral), transforming the spoken letters into words, and/or transforming connected thoughts, words or sentences into coherent expressions or into a written work, such as in forming words or sentences for written works of authorship.

Examples of non-stuttering pathologies that may be suitable for treatment according to operations proposed by the present invention include, but are not limited to, learning disabilities ("LD"), including reading disabilities such as dyslexia, attention deficit disorders ("ADD"), attention deficit hyperactivity disorders ("ADHD") and the like, asphasia, dyspraxia, dysarthria, dysphasia, autism, schizophrenia, progressive degenerative neurological diseases such as Parkinson's disease and/or Alzheimer's disease, and/or brain injuries or impairments associated with strokes, cardiac infarctions, trauma, and the like. In certain embodiments, children having developmental praxia, auditory processing disorders, developmental language disorders or specific language impairments, or phonological processing disorders may be suitable for treatment with methods and/or devices contemplated within the scope of the present invention.

The treatment may be particularly suitable for individuals having diagnosed learning disabilities that include reading disabilities or impairments. A learning disability may be assessed by well-known testing means that establishes that an individual is performing below his/her expected level for age or I.Q. For example, a reading disability may be diagnosed by standardized tests that establish that an individual is below an age level reading expectation, such as, but not limited to, the Stanford Diagnostic Reading Test. See Carlson et al., *Stanford Diagnostic Reading Test* (NY, Harcourt Brace Javanovich, 1976). A reading disability may also be indicated by comparison to the average ability of individuals of similar age. In other embodiments, a relative decline in a subject's own reading ability may be used to establish the presence of a reading disability.

The subject to be treated may have normal hearing sensitivity, typically defined as having pure-tone thresholds at octave frequencies from 250 to 8000 Hz and speech recognition thresholds of $\leq 20$ dB HL (American National Standards Institute, 1996). In other embodiments, the subject may have a hearing impairment.

Figure 2:
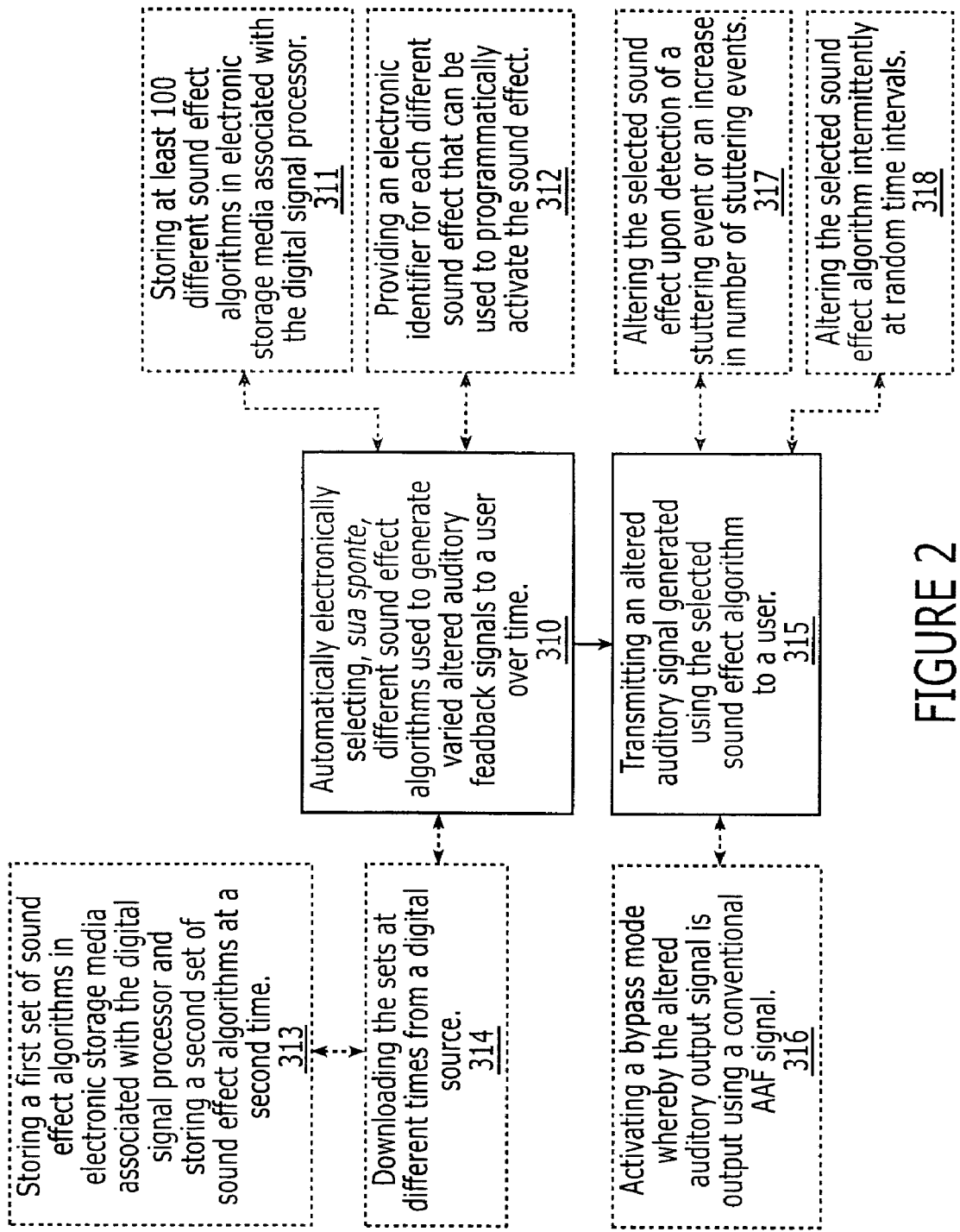
FIG. 2 is a flow diagram of operations that can be carried out to deliver adaptation resistant altered auditory feedback signals to a user according to embodiments of the present invention.

FIG. 2 illustrates operations that can be used to carry out embodiments of the invention. As shown, different signal and/or sound effect algorithms can be automatically electronically selected sua sponte, and the sua sponte selected sound effect(s) can be used to generate varied altered auditory feedback signals to a user over time (block 310). The altered auditory feedback signal generated using the selected signal and/or sound effect algorithm is transmitted to a user (block 315).

In some particular embodiments, at least 100 different sound effect algorithms are stored in electronic storage media associated with a digital signal processor in a portable therapeutic device (block 311). A unique electronic identifier can be provided for each different sound effect and that identifier can be used to programmatically activate/select the associated sound effect (block 312).

In particular embodiments, the device 10 can include at least about 1,000 different programmatically selectable sound effects.

In some embodiments, a first set of sound effect algorithms can be stored in electronic storage media associated with a digital signal processor of a portable treatment device at a first point in time and a second set can be stored at a second point in time (block 313). This will allow a clinician or user to either interchange the second set for the first (save over) or replace or supplement the first set with more alternatives at a later time, or even to add multiple sets (such as upon payment of a surcharge) at an initial set-up. The sets can be downloaded at different times from one or more digital sources (block 314).

Figure 5:
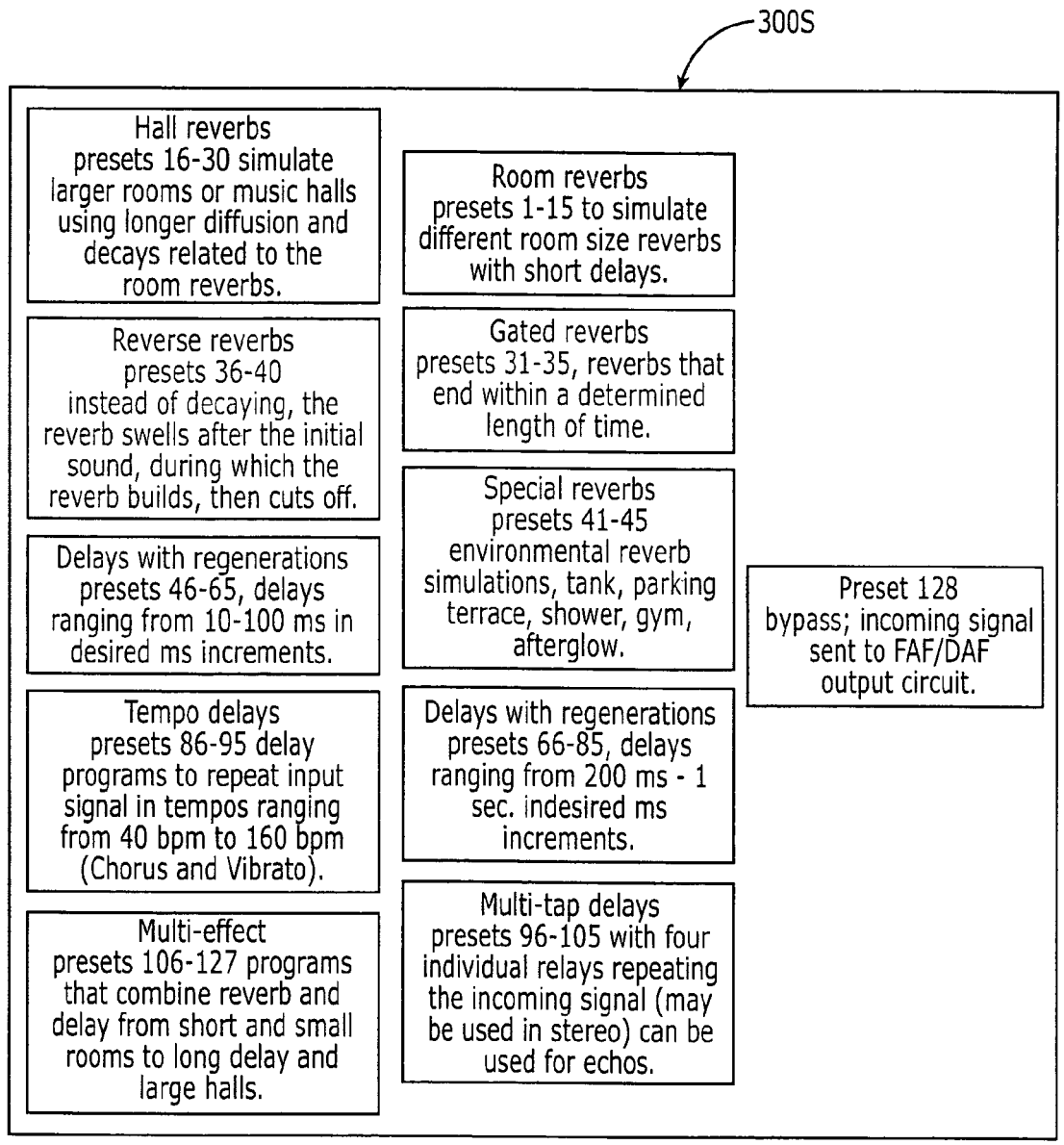
FIG. 5 is a block diagram of examples of selectable sound effects having identifiers according to embodiments of the present invention.
Figure 6:
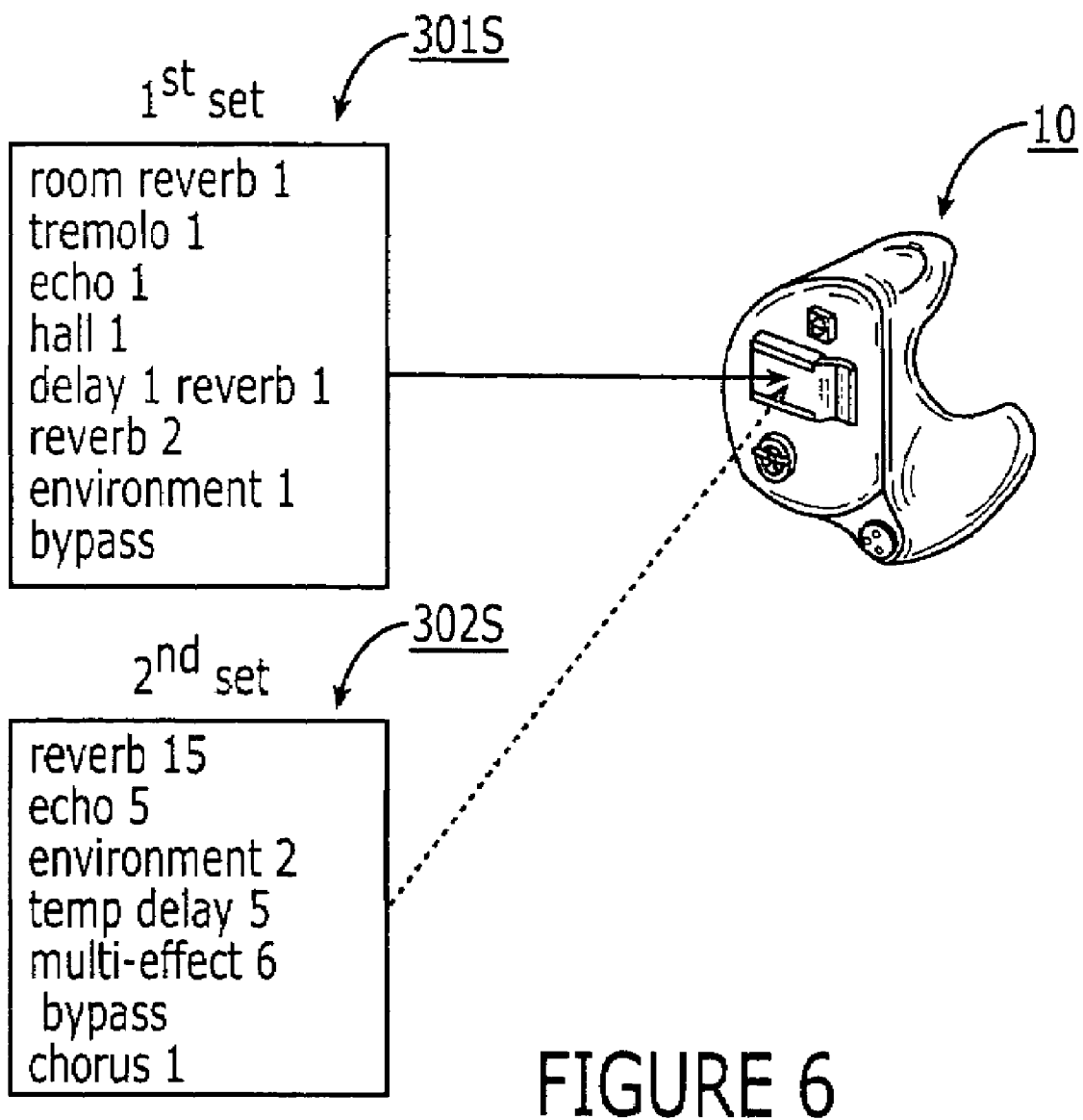
FIG. 6 is a schematic diagram of a portable device configured to digitally accept different sets of sound effects according to embodiments of the present invention.

FIG. 5 illustrates that the sound effects 300S can be configured as predefined algorithms of 128 different program numbers, with general sub-groupings of similar sound effects (indicated by block groups). FIG. 6 illustrates schematically that a first set of sound effects 301S can have a different mix of sound effects, shown as room reverb 1, tremolo 1, echo 1, hall 1, delay 1, reverb 1, reverb 2, environment 1 and bypass. The second set of sound effects 302S can include reverb 15, echo 5, environment 2, tempo delay 5, multi-effect 6, chorus 1 and bypass. The first set 301S may be provided by an OEM or clinician at a first fitting and the second set 302S may be downloaded by the clinician at a second time and/or by a user him or herself using a programmable interface using a digital product (available from a music store or a web site such as may be provided by an OEM of the portable device).

Referring again to FIG. 2, a bypass mode can be activated whereby the altered auditory feedback signal is generated using a conventional AAF signal (block 316). That is, the sound effect selector 300 can either be turned off or configured to activate a circuit or module to generate a conventional AAF signal.

In some embodiments, the selected sound effect can be altered or changed upon detection of a stuttering event or an increase in stuttering events over a target time frame (block 317). The selected sound effect can be altered or changed at random time intervals (block 318).

Figure 3:
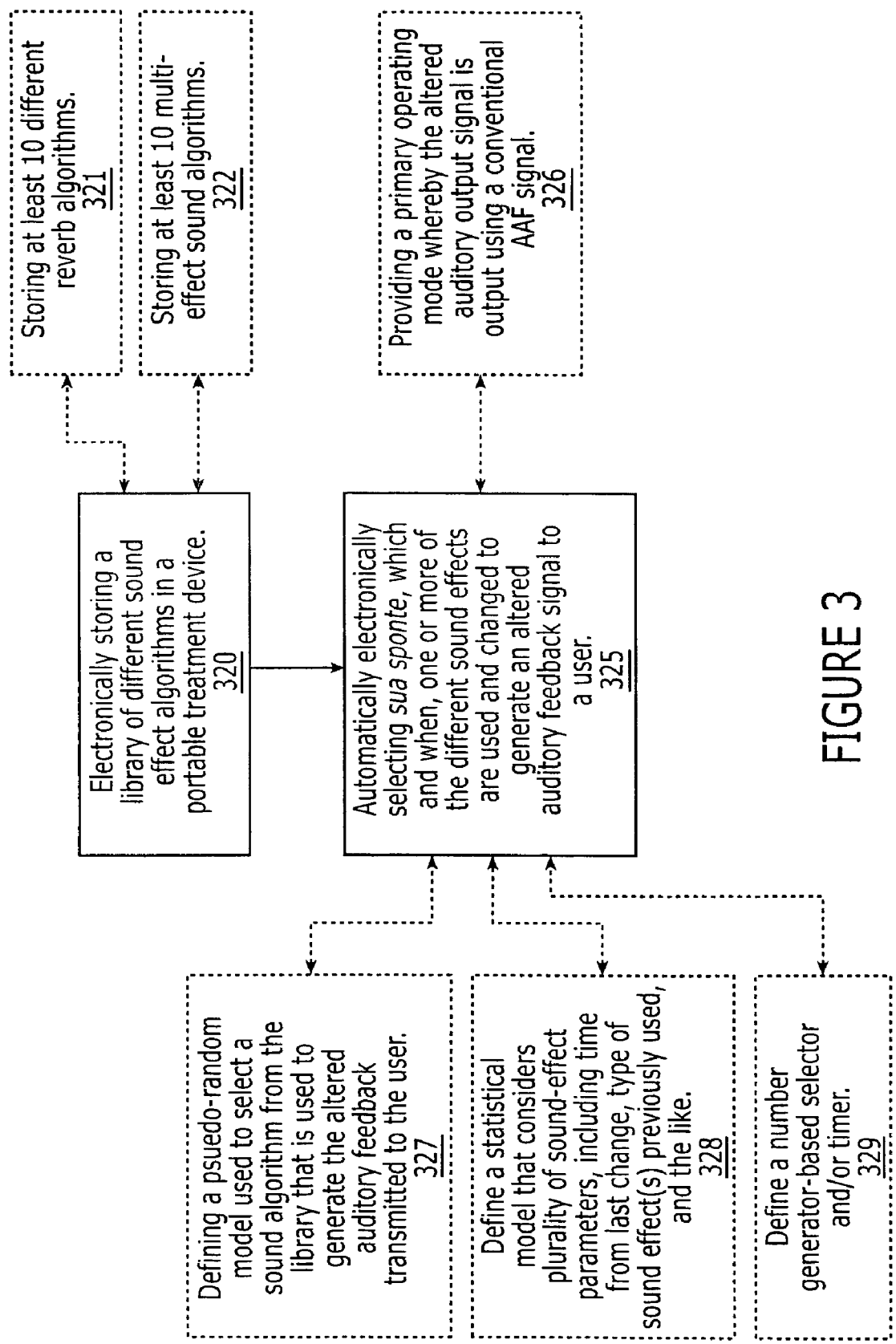
FIG. 3 is a flow diagram of operations that can be carried out to deliver an altered auditory feedback signal using one or more varied signal effects according to embodiments of the present invention.

FIG. 3 illustrates operations that can be carried out to deliver a therapeutic altered auditory feedback signal according to embodiments of the present invention. As shown, a library of electronic sound effect algorithms can be electronically stored in a portable treatment device (block 320). The device can automatically electronically select sua sponte which and when one or more of the different sound effect algorithms is used and for how long, to thereby generate a continuously evolving altered auditory feedback signal to the user (block 325).

The device can store at least about 10 different reverb algorithms (block 321) and/or multi-effect sound algorithms (block 322). A primary operating mode can be provided so that a conventional AAF altered auditory output signal can be generated (block 326). In some embodiments, a pseudo-random model can be defined and used to select a signal effect and/or sound algorithm from the library (block 327). In other embodiments, a multi-parameter statistical model of historical operational data can be used to select the sound effect (block 328). The statistical model can consider one or more of the time from last change, the type of sound effect currently and/or previously used, the stuttering efficacy with respect to signal type, a real-time or trend in number of disfluencies of the user and the like. In yet other embodiments, a random number generator can be used to select the sound effect and/or time to change the selected sound effect (block 329). In other embodiments, a duty cycle can be changed, a signal operational time can be changed, and/or the type of signal effect employed can be automatically changed in a non-random manner.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of a portable therapeutic device, partly on a programmable user interface that communicates with the device and a clinician's computer and/or a user's computer or a remote computer, or as a stand-alone software package. In the latter scenario, the remote computer may be connected to the user's computer through a local area network (LAN) or a wide area network (WAN), or the connection may be made to an external computer (for example, through the Internet using an Internet Service Provider).

The invention is described in part herein with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 4:
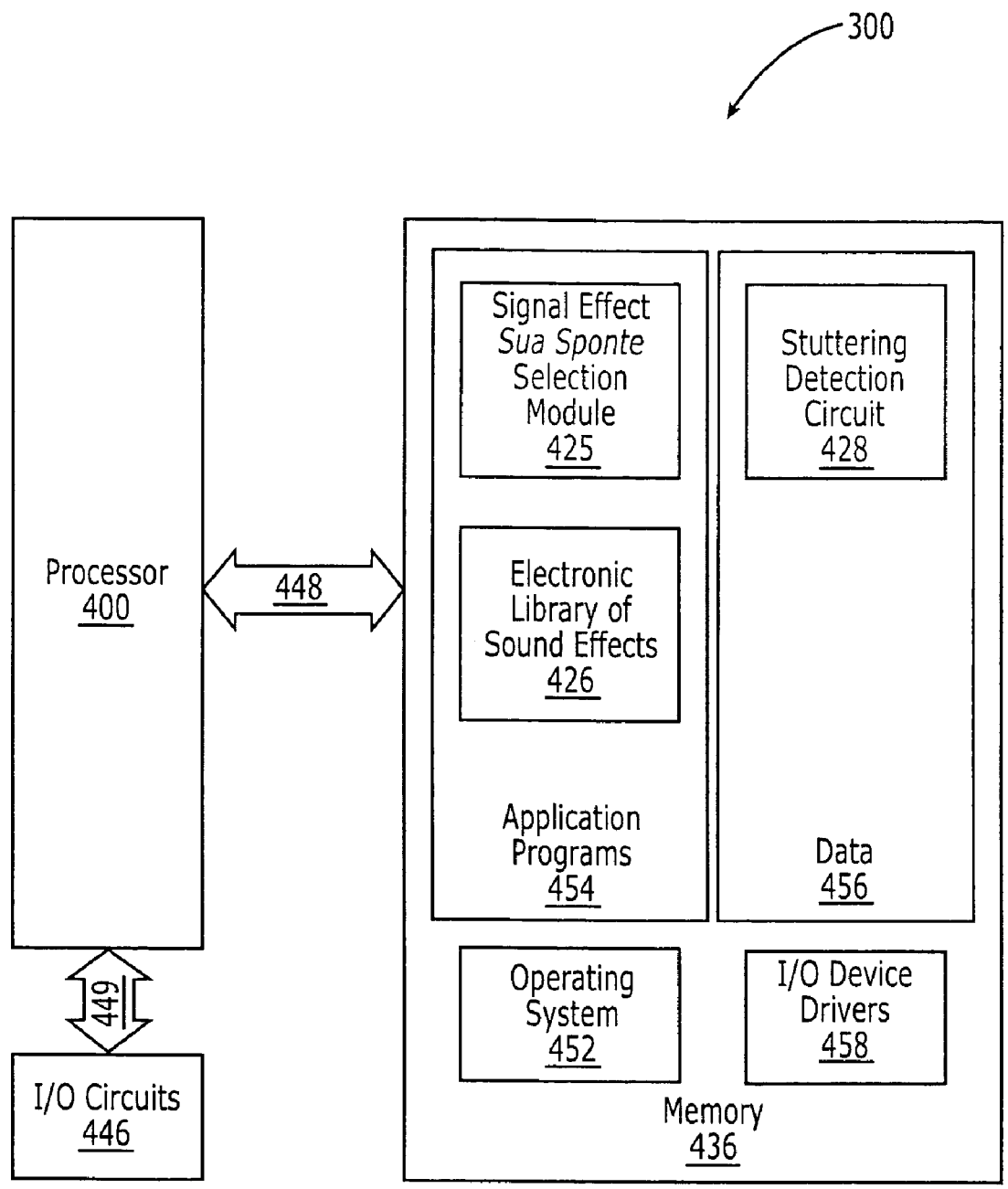
FIG. 4 is a block diagram of a data processing system/computer program according to embodiments of the present invention.

FIG. 4 illustrates an exemplary data processing systems or database environment that may be included in devices operating in accordance with some embodiments of the present invention. As illustrated in FIG. 4, a data processing system, which can be used to carry out or direct operations, includes a processor 400, a memory 436 and input/output circuits 446. The data processing system may be incorporated in, for example, one or more of a portable therapeutic device, a personal computer, programmable interface, server, router or the like. The processor 400 communicates with the memory 436 via an address/data bus 448 and communicates with the input/output circuits 446 via an address/data bus 449. The input/output circuits 446 can be used to transfer information between the memory (memory and/or storage media) 436 and another computer system or a network using, for example, an Internet protocol (IP) or USB connection. These components may be conventional components such as those used in many conventional data processing systems, which may be configured to operate as described herein.

In particular, the processor 400 can be commercially available or custom microprocessor, microcontroller, digital signal processor or the like. The memory 436 may include any memory devices and/or storage media containing the software and data used to implement the functionality circuits or modules used in accordance with embodiments of the present invention. The memory 436 can include, but is not limited to, the following types of devices: cache, ROM, PROM, EPROM, EEPROM, flash memory, SRAM, DRAM and magnetic disk. In some embodiments of the present invention, the memory 436 may be a content addressable memory (CAM).

As further illustrated in FIG. 4, the memory (and/or storage media) 436 may include several categories of software and data used in the data processing system: an operating system 452; application programs 154, 454; input/output device drivers 458; and data 456. As will be appreciated by those of skill in the art, the operating system 452 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 458 typically include software routines accessed through the operating system 452 by the application programs 454 to communicate with devices such as the input/output circuits 446 and certain memory 436 components. The application programs 454 are illustrative of the programs that implement the various features of the circuits and modules according to some embodiments of the present invention. Finally, the data 456 represents the static and dynamic data used by the application programs 454 the operating system 452 the input/output device drivers 458 and other software programs that may reside in the memory 436.

With respect to FIG. 4, the data 456 may include signal parameters and/or sound effect data and/or stuttering event data, time interval change data and the like for use by the circuits and modules of the application programs 454 according to some embodiments of the present invention as discussed further herein.

As further illustrated in FIG. 4, according to some embodiments of the present invention the application programs 454 include one or more of: a Signal Effect Sua Sponte Selection Module 425, and/or a Library of Special Sound Effects 426. The application programs 454 may be located in a local processor and/or database or a remote processor and/or database, or combinations of local and remote databases and/or servers.

While the present invention is illustrated with reference to the application programs 454, 425, 426, in FIG. 4, as will be appreciated by those of skill in the art, other configurations fall within the scope of the present invention. For example, rather than being application programs 425, 426, these circuits and modules may also be incorporated into the operating system 452 or other such logical division of the data processing system. Furthermore, while the application programs in FIG. 4 is illustrated in a single data processing system, as will be appreciated by those of skill in the art, such functionality may be distributed across one or more data processing systems. Thus, the present invention should not be construed as limited to the configuration illustrated in FIG. 4, but may be provided by other arrangements and/or divisions of functions between data processing systems. For example, although FIG. 4 is illustrated as having various circuits and modules, one or more of these circuits or modules may be combined without departing from the scope of the present invention.

Figure 7:
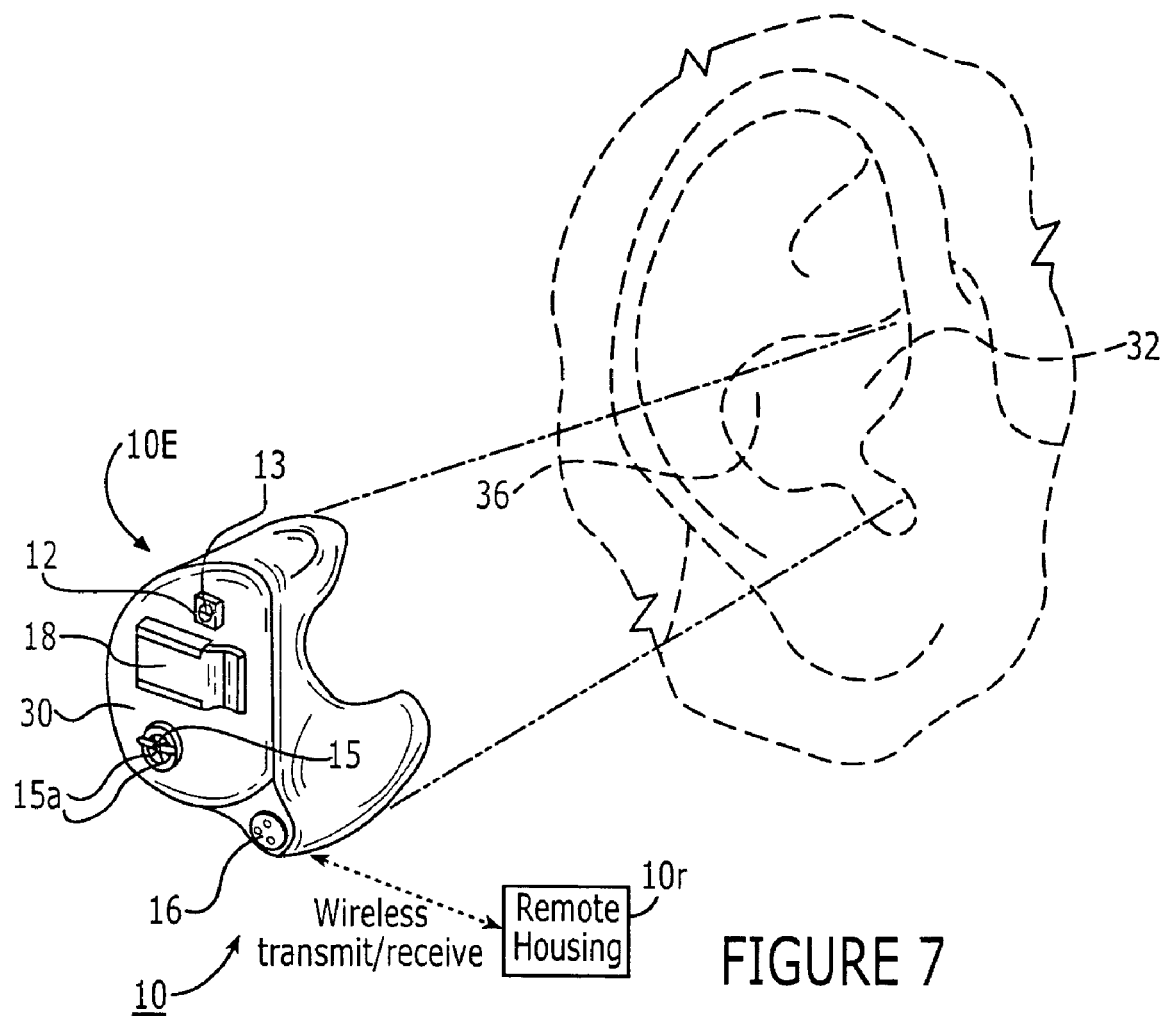
FIG. 7 is a side perspective view of a device configured for in the ear ("ITE") use for treating stuttering and/or communication disorders according to embodiments of the present invention.

Optionally, as shown by the features in broken line in FIG. 7, the device 10 can include a wireless portable remote component 10R (typically sized and configured to fit into a pocket or on a belt and the like) that cooperates with an ear-supported component 10E to provide the desired therapeutic input. As is well known to those of skill in the art, the wireless system configuration may include the ear-mounted component 10E, a processor, which may be held in the remote housing 10H (and/or in the ear-supported housing) and a wireless transmitter that allows the processor to communicate with the ear-mounted component 10E. Examples of wireless head and/or earsets include the Jabra® FreeSpeak Wireless System and other hands-free models that are available from Jabra Corporation located in San Diego, Calif. Examples of hands-free communication devices that employ ear buds, ear hooks, and the like are described in U.S. Pat. Nos. D469,081, 5,812,659 and 5,659,156, the contents of which are hereby incorporated by reference as if recited in full herein.

Figure 8:
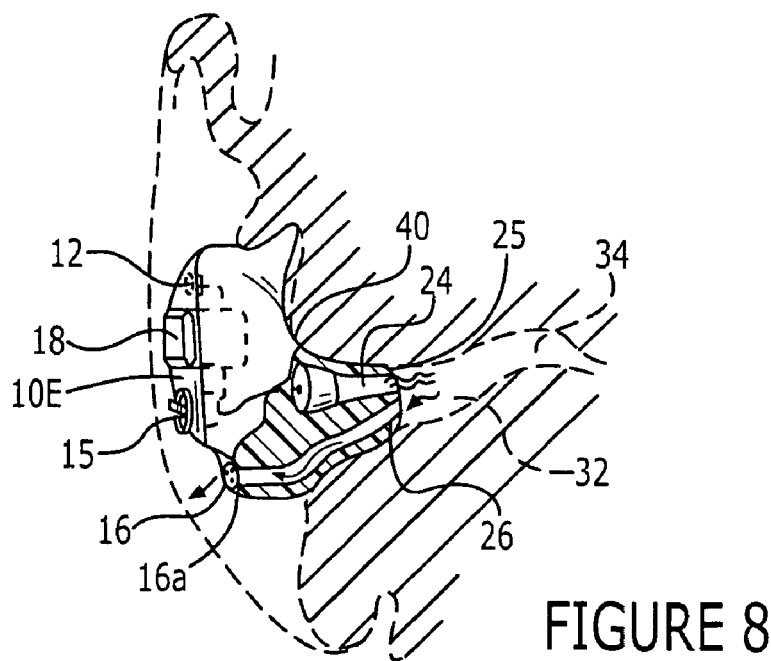
FIG. 8 is a section view of the device of FIG. 7, illustrating its position in the ear canal, according to embodiments of the present invention.

Alternatively, as shown in FIG. 8, the device 10 can be self-contained and supported by the ear(s) of the user. In either a wired, wireless and/or self-contained embodiment, the device 10 can be configured as a portable, compact device with the ear-mounted component being a small or miniaturized configuration. In the description of certain embodiments that follows, the device 10 is described as having certain operating components that administer the altered auditory feedback signal using the selected sound effect. These components may reside entirely in the ear-mounted device 10E or certain components may be housed in the wirelessly operated remote device 10R, where such a remote device is used. Although not shown, the ear or a head mounted component may be wired to a remote member via lead wire. Thus, in yet other embodiments, wired versions of portable feedback systems may be used, typically with a light-weight head mounted or ear-mounted component(s) (not shown). For the remote member configurations, the controller and/or certain delayed auditory feedback signal processor circuitry and the like can be held in the remote housing 10R.

Figure 9:
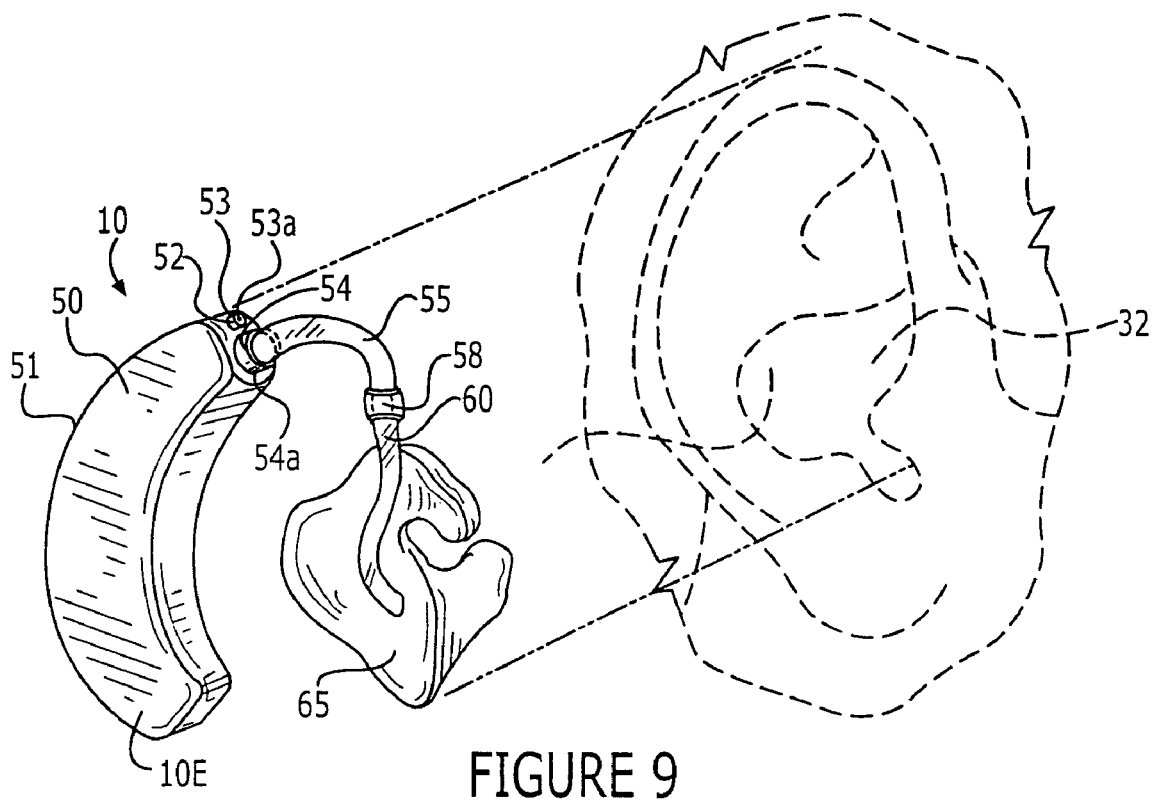
FIG. 9 is a side perspective view of a behind the ear device ("BTE") for treating non-stuttering pathologies according to alternate embodiments of the present invention.
Figure 10:
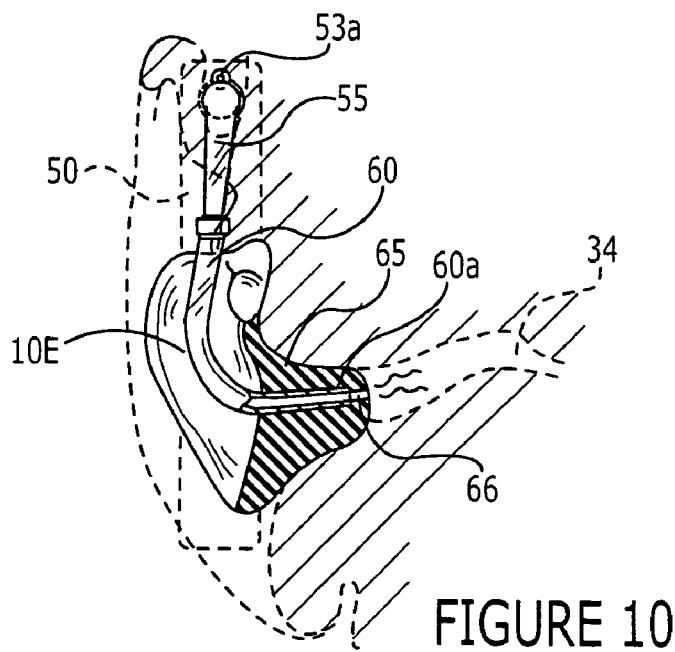
FIG. 10 is a section view of the device of FIG. 9, illustrating the device in position, according to embodiments of the present invention.
Figure 11A:
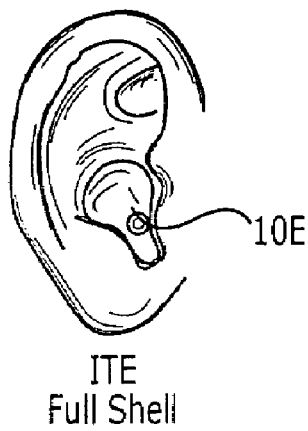
FIGS. 11A-11E are side views of exemplary types of miniaturized configurations that can be used, alone or with another member, to provide the altered auditory feedback signal according to embodiments of the present invention.
Figure 11B:
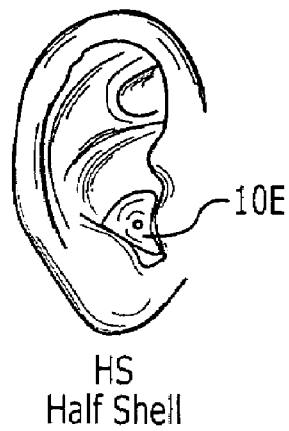
Figure 11C:
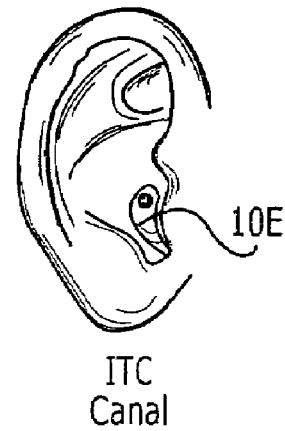
Figure 11D:
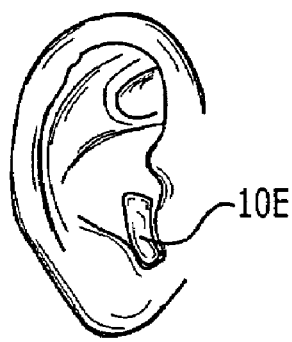
Figure 11E:
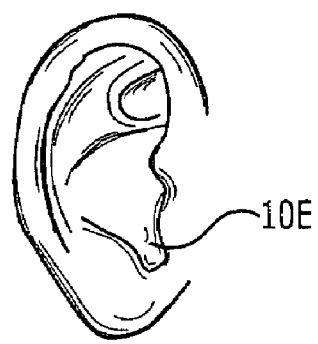

In certain embodiments, as shown in FIGS. 7-11, the FAF treatment may be provided by a minimally obtrusive device 10 that is configured with an ear supported component 10E. As such, the device 10 can be configured as a portable, compact device with a small or miniaturized ear-supported housing. FIGS. 7, 8 and 11A illustrate that the device 10 and/or ear component 10E of the device can be configured as an in-the-ear ("ITE") device. FIGS. 9 and 10 illustrate that the device 10 can include a behind-the-ear ("BTE") device. FIGS. 11B-11E illustrate various suitable configurations of ear-supported housings/devices. FIG. 11C illustrates an in-the-canal ("ITC") version, and FIG. 11B illustrates a "half-shell" ("HS") version of an ITC configuration. FIG. 11D illustrates a mini-canal version ("MC") and FIG. 11E illustrates a completely-in-the-canal ("CIC"). The CIC configuration can be described as the smallest of the ear-supported devices and is largely concealed in the ear canal.

As will be discussed in more detail below, in certain embodiments, the therapeutic device 10 for treating non-stuttering pathologies or disorders includes a small, typically miniaturized, housing which contains a power source, a signal processor including a receiver, an FAF circuit, and a transmitter therein. The housing can be configured and sized to be worn positioned proximate the ear and does not require wires or cables to external remote components during use. Certain components, such as a receiver or transducer, may be located away from the ear canal, although typically still within relatively close proximity thereto.

As discussed with respect to FIG. 1, generally described, in operation, the portable device 10 receives input sound signals from a patient at a position in close proximity to the ear (such as via a microphone in or adjacent the ear), processes the signal to generate an altered auditory feedback signal 399 using a selected sound effect (indicated by element 301-30N where "N" represents the possible number of sound effects selectable), amplifies the signal, and delivers the processed signal into the ear canal of the user.

Referring now to FIG. 7, as illustrated, the ITE device 10 can be a single integrated unit that is self-contained and does not require wires and/or remote devices for operational use or may be a wireless device 10 that includes an ITE component. The device 10 includes a housing 30 of which at least a portion is configured and sized to be able to be received into the ear canal 32 and positioned close to the eardrum 34. The housing 30 can include a proximal portion which is insertable a predetermined distance into the ear canal 32 and is sized and configured to provide a comfortable, snug fit therein. The material of the housing 30 can be formed of a hard or semi-flexible elastomeric material such as a polymer, copolymer, or derivative or mixture thereof.

It is also noted that although the device 10 is shown throughout as a single unit in one ear, in certain embodiments, the user may employ two (binaural) discrete devices 10, with one ear-supported component in/on each ear (not shown) such that that they work in concert or independently of the other. The two ear-mounted components may be operatively in communication via a wireless communication mode or wired, such as with a thin, light-weight and minimally obtrusive cable having a length sufficient to extend between the two devices when in position in or adjacent their respective ears.

In some embodiments, the two devices 10 can be configured so that the altered auditory feedback signal generated can be coordinated with each device cooperating with the other. One of the devices 10 may be a master and the other the slave, or a remote device can operate or communicate with each of the ear-mounted devices to coordinate the sound effect and timing of the changes to the altered auditory feedback signal.

As shown in FIGS. 7 and 8, a distal portion of the device 10 can include a receiver 12, a receiver inlet 13, an accessory access door 18, a volume control 15, and a small pressure equalization vent 16. It is noted that throughout the description, the devices may employ, typically in lieu of a volume control 15, automated compression circuitry such as a wide dynamic range compression ("WDRC") circuitry. In operation, the circuitry can automatically sample incoming signals and adjust the gain of the signal to lesser and greater degrees depending on the strength of the incoming signal. The receiver 12, such as a transducer or microphone, can be disposed in a portion of the housing 30 that is positioned near the entrance to the ear canal 36 so as to receive sound waves with a minimum of blockage. More typically, the receiver 12 is disposed on or adjacent a distal exterior surface of the housing 30 and the housing 30 optionally includes perforations 13 to allow uninhibited penetration of the auditory sound waves into the receiver or microphone.

As shown, the device 10 may also include an accessory access panel, shown in FIGS. 7 and 8 as a door member 18. The door member 18 can allow relatively easy access to the internal cavity of the device 10 so as to allow one to interchange batteries, or to repair electronics, to accept a programmable interface and the like. Further, this door member 18 can also act as an "on" and "off" switch such that the device 10 can be activated or deactivated by opening and closing the door 18. The device 10 can further include a volume control that is also disposed to be accessible by a patient. As shown, the device 10 may include raised gripping projectiles 15a for easier adjustment.

The proximal side of the device 10 can hold the transmitter or speaker 24. The housing 30 can be configured to generally fill the concha of the ear 40 to prevent or block un-delayed signals from reaching the eardrum. As shown in FIG. 8, the proximal side of the housing 30 includes at least two openings 25, 26. A first opening is a vent opening 26 in fluid communication with the pressure vent 16 on the opposing side of the housing 30. As such, the vent openings 16, 26 can be employed to equalize ear canal and ambient air pressure. The distal vent opening 16 can also be configured with additional pressure adjustment means to allow manipulation of the vent opening 16 to a larger size. For example, a removable insert 16a having a smaller external aperture can be configured to be received into a larger aperture in the vent. Thus, removal of the plug results in an "adjustable" larger pressure vent opening 16.

Still referring to FIG. 8, a second opening, a sound bore 25 is disposed so as to face into the ear canal on the proximal side of the device and can deliver the digitally processed signal to the inner ear canal. The sound bore 25 may be free of an intermediate covering(s), permitting free, substantially unimpeded delivery of the processed signal to the inner ear. Alternatively, a thin membrane, covering, or baffle (not shown) may be employed over the sound bore 25 to protect the electronics from unnecessary exposure to biological contaminants.

If desired, the housing 30 may contain a semi-flexible extension over the external wall of the ear (not shown) to further affix the housing 30 to the ear, to provide additional structure and support or to hold components associated with the device 10, such as power supply batteries. The operative electronic circuitry may be powered by one or more internally held power sources, such as a miniaturized battery of suitable voltage.

An alternative embodiment of the device 10 shown in FIGS. 7 and 8 is illustrated in FIGS. 9 and 10 with a BTE device. As illustrated, the device 10 includes a standard hearing aid type shell or housing 50, an ear hook 55, and an ear mold 65. The ear mold 65 is flexibly connected to the ear hook by mold tubing 60. The mold tubing 60 is sized to receive one end of the ear hook 58. The ear hook 55 can be formed of a stiffer material than the tubing 60. Accordingly, an end portion 58 of the ear hook 55 is inserted into the end of the mold tubing 60 to attach the components together. The opposing end portion 54 of the ear hook 55 is attached to the housing 50. The ear hook end portion 54 can be threadably engaged to a superior or top portion of the housing 50.

As shown in FIGS. 9 and 10, the ear mold 65 is adapted for the right ear but can easily be configured for the left ear. The ear mold 65 is configured and sized to fit securely against and extend partially into the ear to structurally secure the device 10 to the ear. The tubing proximal end 60a extends a major distance into the ear mold 65, and more typically extends to be slightly recessed or substantially flush with the proximal side of the ear mold 65. The tubing 60 can direct the signal and minimize the degradation of the transmitted signal along the signal path in the ear mold.

Still referring to FIGS. 9 and 10, the proximal side of the ear mold 65 can include a sound bore 66 in communication with the tubing 60. In operation, the signal is processed in the housing 50 and is transmitted through the ear hook 54 and tubing 60 into the ear mold 65 and is delivered to the ear canal through the sound bore 66. An opening can be formed in the housing 50 to receive the auditory signal generated by the patient's speech. As shown in FIG. 9, the opening is in communication with an opening in a receiver such as a microphone 53 positioned on the housing. The receiver or microphone 53 can be positioned in an anterior-superior location relative to the wearer and extend out of the top of the housing 50 so as to freely intercept and receive the signals.

Corrosion-resistant materials, such as a gold collar or suitable metallic plating and/or biocompatible coating, may be included to surround the exposed component in order to protect it from environmental contaminants. The microphone opening 53a can be configured so as to be free of obstructions in order to allow the signal to enter unimpeded or freely therein.

Additionally, the housing 50 can employ various other externally accessible controls (not shown). For example, the anterior portion of the housing 51 can be configured to include a volume control (and/or compression circuitry such as WDRC), an on-off switch, and a battery door. The door can also provide access to an internal tone control and various output controls. Optionally, the BTE device can include an external port that engages an external peripheral device such as a pack for carrying a battery or for trickle charging the battery, where long use or increased powering periods are contemplated, or for recharging the internal power source. In addition, the device 10 may be configured with a port interface to allow interrogation or programming via an external source and may include cabling and adaptor plug-in ports to allow same. For example, as will be discussed further below, the device 10 can be releasably attachable to an externally positioned signal processing circuitry for periodic assessment of operation, adjustment or link to an external evaluation source or clinician.

The external pack and/or remote housing 10R, when used, may be connected to the housing (not shown) and configured to be light weight and portable, and preferably supportably attached to or worn by a user, via clothing, accessories, and the like. In other embodiments the remote housing or pack may be stationary during use, depending on the application and desired operation.

In position, with the ear mold 65 in place, the BTE device 10 is disposed with the ear hook 55 resting on the anterior aspect of the helix of the auricle with the body of the housing 50 situated medial to the auricle adjacent to its attachment to the skull. Typically, the housing 50 is configured to follow the curve of the ear, i.e., it is a generally elongated convex. The ear-mounted housing size can vary, but can be sized from about 1 inch to 2.5 inches in length, measured from the highest point to the lowest point on the housing 50. The ear hook 55 is generally sized to be about 0.75 to about 1 inch for adults, and about 0.35 to about 0.5 inches for children; the length is measured with the hook 55 in the radially bent or "hook" configuration.

In certain embodiments, the receiver 53 (i.e., the microphone or transducer) is positioned within a distance of about 1 cm to 7 cm from the external acoustic meatus of the ear. The transducer may be positioned within 4 cm of the external acoustic meatus of the ear, and typically the transducer is positioned within about 2.5 cm. It is noted that the embodiments illustrated are a single, integrated housing unit that holds the power source and operational circuitry in a minimally obtrusive configuration, thereby allowing the device to be conveniently and advantageously held in use adjacent and/or in the ear.

Referring to FIGS. 11A-11E, in particular embodiments, the device 10 can include or be an ITE device (i.e., full shell, half shell, ITC, MC, or CIC device) positioned entirely within the concha of the ear and/or the ear canal. In other embodiments, as shown in FIG. 9, the device 10 can include or be configured as a BTE device that is partially affixed over and around the outer wall of the ear so as to minimize the protrusion of the device beyond the normal extension of the helix of the ear.

Hearing aids with circuitry to enhance hearing with a housing small enough to either fit within the ear canal or be entirely sustained by the ear are well known. For example, U.S. Pat. No. 5,133,016 to Clark discloses a hearing aid with a housing containing a microphone, an amplification circuit, a speaker, and a power supply, that fits within the ear and ear canal. Likewise, U.S. Pat. No. 4,727,582 to de Vries et al. discloses a hearing aid with a housing having a microphone, an amplification circuit, a speaker, and a power supply that is partially contained in the ear and the ear canal, and behind the ear. Each of the above-named patents is hereby incorporated by reference in its entirety as if fully recited herein. For additional description of a compact device used to ameliorate stuttering, see U.S. Pat. No. 5,961,443, the contents of which are hereby incorporated by reference as if recited in full herein.

In certain embodiments, the altered auditory feedback signal is provided by digital signal processing technology with programmably selectable operating parameters that can be customized to the needs of a user and adjusted at desired intervals such as monthly, quarterly, annually, and the like, typically by a clinician or physician evaluating the individual.

The patient fitting can include selecting the desired sound effects (such as, but not limited to, those shown in Table I), adjusting any of the parameters associated with the sound effects and/or the duration, duty cycle and the like.

The patient fitting can be carried out with programmably selectable and/or adjustable operating parameters such as (but not limited to)+/− shifts in FAF (typically in about 500 Hz-200 Hz increments), linear gain control (such as about four 5-dB step size increments), independent or individually adjustable "n" band gain controls (where n can be between about 2-20 bands with center frequencies ranging from 250-7000 Hz with 20 dB gain control settings), pitch delay, other delays, low pass filter range, masking noise, amplitude and the like.

The fitting can be carried out to also select desired sound effects that will be used during operation and that may be particularly suitable for the particular user (or sets of sound effects as noted above). In other embodiments, the sound effects can be defined based on a standardized program of one or more sets of sound effects.

Further, in particular embodiments, the device 10 can be configured to provide sound effect feedback signals and also selectably provide conventional AAF (such as one or more of FAF, DAF and MAF). The delays for DAF may be provided with an adjustably selectable delay time of between about 0-128 ms and the programmable interface and the internal operating circuitry and/or the signal processor, which may be one or more of a microprocessor or nanoprocessor, can be configured to allow adjustable and/or selectable operational configurations of the device to operate in the desired feedback mode or modes. For additional description of a compact device used to ameliorate stuttering, see Stuart et al., *Self-Contained In-The Ear Device to Deliver Altered Auditory Feedback: Applications for Stuttering*, Annals of Biomedical Engr. Vol. 31, pp. 233-237 (2003), the contents of which are hereby incorporated by reference as if recited in full herein.

The FAF frequency shift or adjustment can be any desired shift, but is typically within about +/−2 octaves from the frequency of the detected auditory speech signal of the user. In certain embodiments, the frequency is adjusted at least about +/−⅛ of an octave, and typically the frequency can be adjusted at least about +/−¼ of an octave from the detected auditory signal. In particular embodiments, the frequency altered feedback signal can be adjusted so as to provide a frequency shift of at least about +/−½ of an octave, while in other embodiments, the frequency shift is at about +/−¾ to 1 octave. Other shifts, or multiples thereof, and/or different increments of octave shift, may be employed.

The frequency shift, measured in hertz, will typically be dependent upon the input signal. For example, for a 500 Hz input signal, a one-octave shift is about 1000 Hz; similarly, a one octave shift of a 1000 Hz input signal is about 2000 Hz.

Adjustments of the default parameters associated with a selected sound effect algorithm may also be adjusted from a normal or default configuration.

In a conventional AAF (particularly DAF and FAF) operating mode, the device 10 be configured to be substantially "acoustically invisible" so as to provide the high fidelity of unaided listening and auditory self-monitoring while at the same time delivering optimal altered feedback, e.g, a device which can substantially maintain a relatively normal speech pattern. However, in certain sound effect modes, the signal may not be acoustically invisible and may provide a relatively abnormal speech pattern for a period of time. The period of time the more dominant sound effect is employed may be a short period of time, such as less than about 30 minutes, typically less than about 15 minutes, and may be less than about 5 minutes.

The adjustment may be customized based on one or more of the particular disorder of the patient and/or the patient's response to a plurality of different "test" sound effects as well as "test" conventional AAF settings during a set-up evaluation based on an improvement in stuttering or readability (for non-stuttering disorders) to evaluate the efficacy of the response. In addition, the frequency and/or delay adjustment may be altered over time upon periodic clinical evaluations.

As described above, the device 10 can be compact and portable. As such, it does not require remotely located components for normal operational use. The present invention now provides for a portable and substantially non-intrusive device that allows for periodic or "chronic" use. As such, the portable device 10 can be allowed for ongoing use without dedicated remote loose support hardware. The device may employ a microphone that is held proximate the ear. That is, the present invention provides a readily accessible communication enhancing (reading assist) instrument that, much like optical glasses or contacts, can be used at will, such as only during planned or actual reading periods when there is a need for remedial intervention to promote reading ability.

FIG. 12A illustrates an example of a circuit 90 for device 10 that can be used to generate the altered auditory feedback signal using a selectable sound effect. As shown, the circuit 90 includes a receiver 70, a low pass filter 72, an ADC (Analog to Digital Converter) 76, a sound effect selector 300 and sound effect algorithms 300S, an optional voice sample comparator 80, a DAC (Digital to Analog Converter) 82, a low pass filter 84, an adjustable gain amplifier 86 and a speaker 24. The circuit 90 has a programmable interface 100.

FIG. 12B is another example of a circuit 90 for device 10 that can be used to generate the altered auditory feedback signal using a selectable sound effect. As shown, the circuit 90 includes a receiver 70, a low pass filter 72, a sample and hold circuit 74, an ADC converter 76, a sound effect selector 300 with a set of selectable sound effect algorithms 300S (301-30N), a voice comparator 80, a frequency alteration circuit 78, a DAC converter 82, a low pass filter 84, an adjustable gain amplifier 86 and a speaker 24.

As shown in FIGS. 12A, 12B, 13A and 13B, in certain embodiments, the device 10 includes a digital signal processor (DSP) that is configured with at least the speaker 24, the A/D converter 76, an attenuator, and the receiver 70. The selector module 300 with the programmable sound effects 300S can be held in memory and incorporated into a digital signal processor (DSP) micro (or nano) processing chip. An exemplary miroprocessing chip is available from MICRO-DSP, a Canadian Corporation, as will be discussed further below. The DSP may be especially important in devices directed to users desiring minimally obtrusive devices that do not unduly interfere with normal life functions. Beneficially, allowing day-to-day or at will ("on-demand") periodic use may improve stuttering or for communication impairments, reading ability (i.e., comprehension, speed and the like). Further, the compact device permits on-going or more "chronic" availability for therapeutic intervention.

FIG. 12B illustrates a schematic diagram of a device 10 having a circuit employing an exemplary signal processor 90 (DSP) with a software programmable interface 100. The broken line indicates the components may, in certain embodiments, be commonly held in or on a miniaturized device 10 such as, but not limited to, the ITC, ITE, or CIC devices described above. Generally described, the signal processor circuit 90 receives a signal generated by a user's speech; the signal is analyzed and either altered using a selected sound effect or using a frequency shift (for FAF mode) according to predetermined parameters. Finally, the feedback signal is transmitted into the ear canal of the user.

In operation, in certain embodiments, referring again to FIG. 12B, the receiver 70 such as a microphone or transducer receives the sound waves. The receiver 70 produces an analog input signal of sound corresponding to the user's speech. According to the embodiment shown in FIG. 12B, the analog input signal is converted to a stream of digital input signals. Prior to conversion to a digital signal the analog input signal is filtered by a low pass filter 72 to prevent or inhibit aliasing. The cutoff frequency for the low pass filter 72 should be sufficient to reproduce a recognizable voice sample after digitalization. A conventional cutoff frequency for voice is about 8 kHz. Filtering higher frequencies may also remove some unwanted background noise. The output of the low pass filter 72 can be input to a sample and hold circuit 74. As is well known in the art, the sampling rate should exceed twice the cutoff frequency of the low pass filter 72 to inhibit or prevent sampling errors. The sampled signals output by the sample and hold circuit 74 can be input into an ADC 76. The digital signal stream representing each sample is then fed into a sound effect alteration circuit 300 and/or a frequency shift alteration circuit 78. The frequency shift circuit 78 may be embodied in multiple ways, including incorporated into the sound effect selector module 300, as is known to one of ordinary skill in the art.

Still referring to FIG. 12B, the output of the frequency shift circuit 78 can then be fed into a DAC 82. The analog signal out of the DAC 82 may then passed through a low pass filter 84 (this step may be appropriate for an FAF/DAF mode to more accurately reproduce the FAF of the original signal). The output of the low pass filter 84 is fed into an adjustable gain amplifier 86 to allow the user (or a clinician) to adjust the output volume of the device. Finally, the amplified analog signal is connected to a speaker 24. The speaker 24 will then recreate an altered auditory feedback version of the user's spoken words.

Figure 13A:
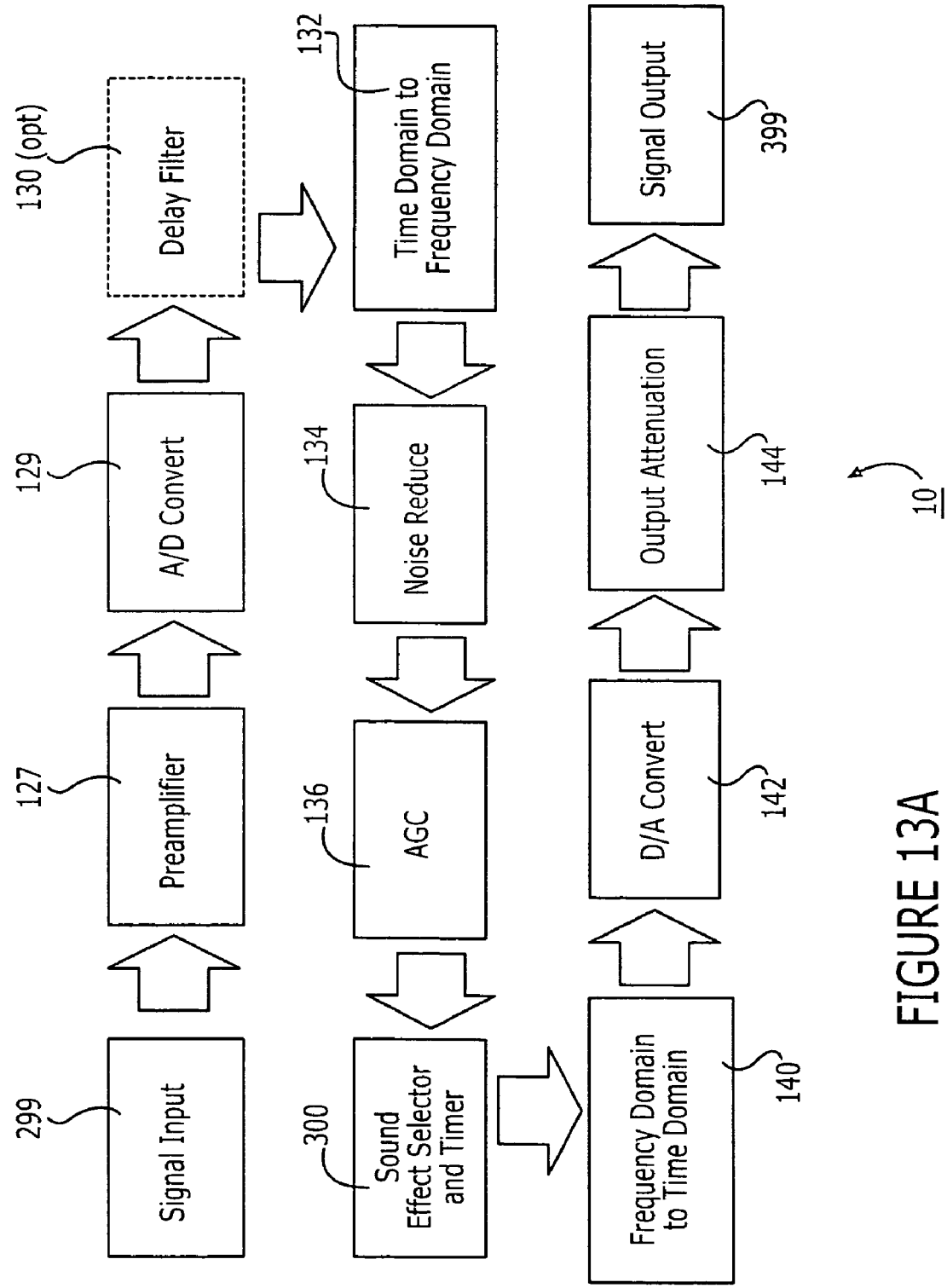
FIG. 13A is a schematic illustration of a programmable (selectable frequency shift) altered auditory feedback system for a miniaturized compact BTE, ITE, ITC, or CIC device, or the like, according to embodiments of the present invention.

Other exemplary operations/features or components that may be used to carry out the treatments contemplated by embodiments of the present invention are illustrated in FIG. 13A. As before, an input signal 299 is received, directed through a preamplifier(s) 127, then through an ADC 129, and optionally through a delay filter 130. The delay filter 130 may be used where DAF or combinations of FAF/DAF are desired or where sound effects may employ delays. The digital signal can be converted from the time domain to the frequency domain 132, passed through a noise reduction circuit 134, and then through compression circuitry such as an AGC 136 or WDRC. The selected sound effect from the signal effect selector 300 is applied to the signal to provide the altered feedback signal 138, the altered feedback signal is reconverted to the time domain 140, and passed through a DAC 142, then an output attenuator 144, culminating in output of the altered auditory feedback signal 399.

In operation, the illustrated operations may be programmably sua sponte selected, activated, timed, or adjusted to provide the desired change in output, i.e., the altered auditory feedback signal. The operations shown can be carried out in and/or with a miniaturized compact BTE, ITE, ITC, or CIC device, and the like, according to embodiments of the present invention.

Figure 13B:
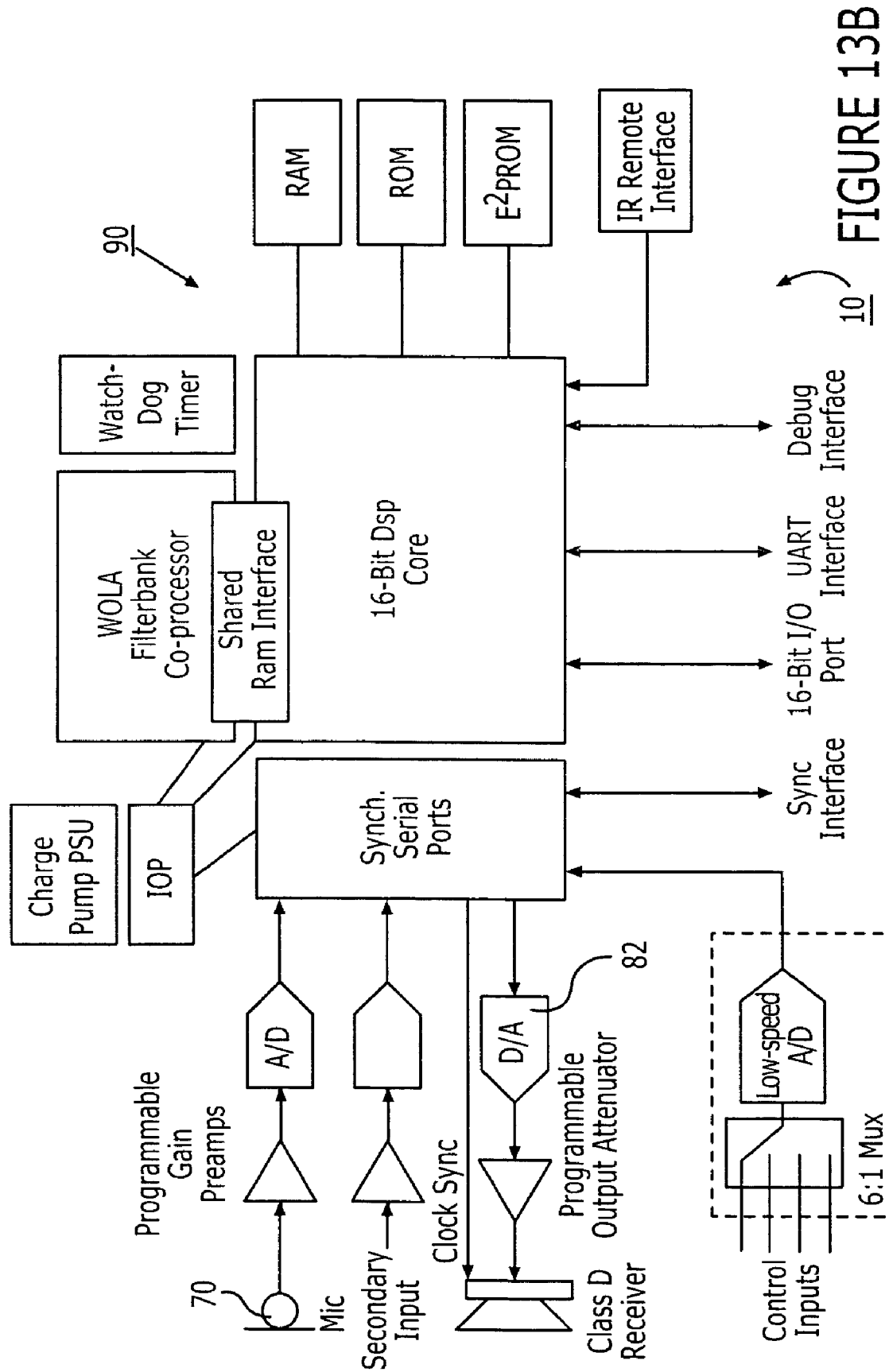
FIG. 13B is a schematic illustration of an exemplary DSP (digital signal processing) architecture that can be used to generated altered auditory feedback according to embodiments of the present invention.

FIG. 13B is a schematic illustration of the architecture of a known programmable DSP 90 that may be particularly suitable for generating the sound effect and FAF-based treatments, as it is particularly suitable for compact devices. This DSP architecture is known as the Toccata™ system and is available from MICRO-DSP TECHNOLOGY CO., LTD., a subsidiary of INTERNATIONAL AUDIOLOGY CENTRE OF CANADA INC. As shown, the Toccata DSP technology supports a wide-range of low-power audio applications and is believed to be the first software programmable chipset made generally available to the hearing aid industry. Generally described, with reference to FIG. 13B, by incorporating a 16-bit general-purpose DSP(RCore), a Weighted Overlap-Add (WOLA) filterbank coprocessor and a power-saving input/output controller, the Toccata™ chipset offers a practical alternative to traditional analog circuits or fixed function digital ASICs. Two 14-bit A/D and a 14-bit D/A can be used to provide high-fidelity sound. Toccata's flexible architecture makes it suitable to implement a variety of algorithms, while employing low power consumption, high fidelity, and a compact or small size. Exemplary features of the Toccata™ DSP technology include: (a) miniaturized size; (b) very low-power, about 1.5 volts or less operation; (c) low-noise, (d) 14-bit A/Ds & amp; (e) D/A interface to industry-standard microphones; (f) Class D receivers and telecoils; (g) RCore: 16-bit software-programmable Harvard architecture DSP; (h) configurable WOLA filterbank coprocessor efficiently implements analysis filtering, gain application; and (i) synthesis filtering. Exemplary performance specifications of the Tocatta™ technology DSP are described in Table 2.

TABLE 2

| Parameter | |
|---|---|
| Operation Voltage | 1.2 V |
| Current Consumption[1] | 1 mA |
| Input/Output Sampling Rate | 32 kHz |
| Frequency Response | 200-7000 Hz |
| THD + N (at −5 dB re: Digital Full Scale) | <1% |
| Programmable Analog Preamplifier Gain | 18, 22, 28 dB |
| Programmable Digital Gain | 42 dB |
| Programmable Analog Output Attenuation | 12, 18, 24, 30 dB |
| Equivalent Input Noise | 24 dB |

[1]may be algorithm dependent

For a conventional dual FAF/DAF output, the device 10 may have an adjustable delay operatively associated with the auditory delay circuit 130 (FIG. 13A). In such an embodiment, the delay circuit 130 can include a detector that detects a number of predetermined triggering events within a predetermined time envelope. Where desired, a delay circuit or wave signal processor can be placed serially in line with the selector module 300 or the FAF circuit in FIG. 12B and, as shown in FIG. 12B, can include a voice sample comparator 80 for comparing a series of digitized voices samples that may be input to the circuit and output from the delay circuit. As is known in the art, digital streams can be compared utilizing a microprocessor. The voice sample comparator 80 can output a signal to the sound effect selector module 300 to provide data or notify when a change in sound effect may be appropriate based on the number of disfluencies, a relative increase in disfluencies and/or when an abnormal speech rate detected.

Alternatively, or additionally, the voice sample comparator 80 can signal the delay circuit or sound effect selector 300 to increase or decrease the time delay or select a different sound or signal effect depending on the desired speech pattern, or the number of disfluencies and/or abnormal speech rate detected.

The device 10 may also have a switching circuit (not shown) to interrupt transmission from the microphone to the earphone, i.e, an activation and/or deactivation circuit. One example of this type of circuit is disclosed in U.S. Pat. No. 4,464,119 to Vildgrube et al., column 4, (see generally lines 40-59 et seq.), which is hereby incorporated herein by reference. The device 10 can be configured to be interrupted either by manually switching power off from the batteries, or by automatic switching when the user's speech and corresponding signal input falls below a predetermined threshold level. This can inhibit sounds other than the user's speech from being transmitted by the device.

Alternatively, as is known in the art, other delay circuits can be employed such as, but not limited to, an analog delay circuit like a bucket-brigade circuit.

Each of the circuit components and/or operations described herein, as is known in the art, can be interchanged with other discrete or integrated circuit components to generate sua sponte altered auditory feedback signals over time as contemplated by embodiments of the present invention.

Figure 14:
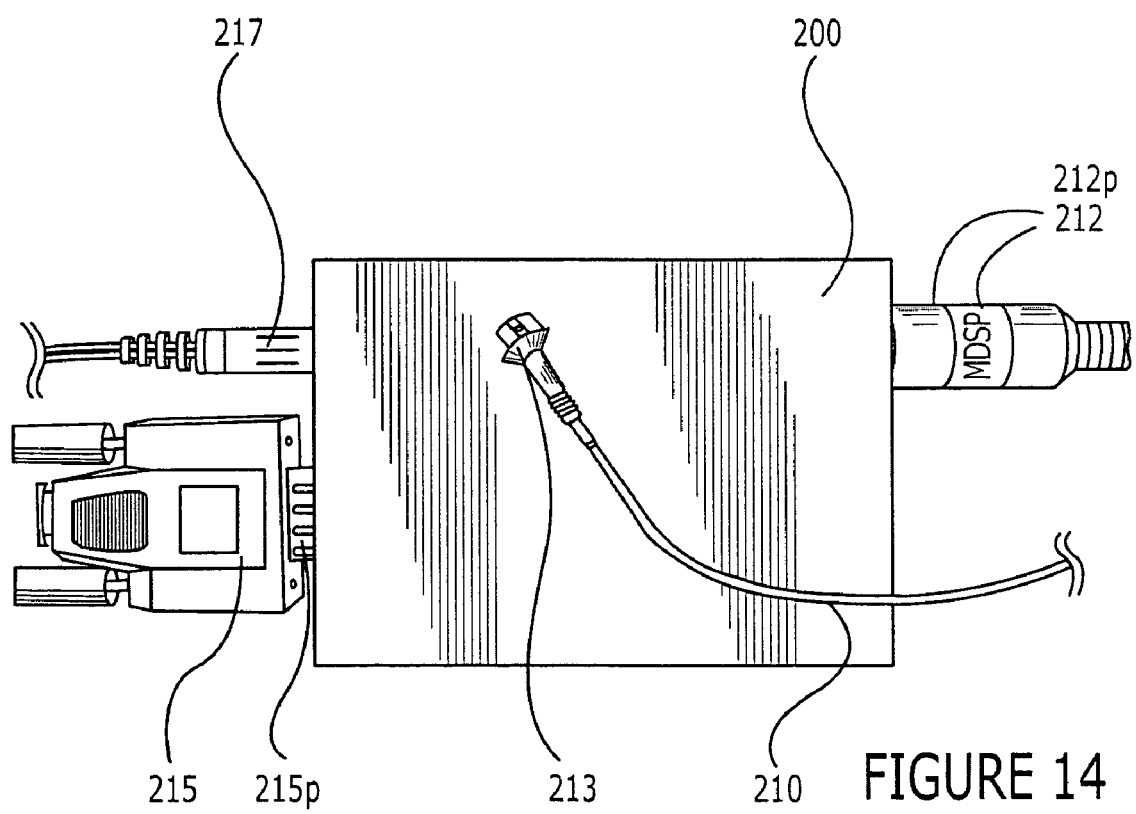
FIG. 14 is top view of an example of a programming interface device to provide communication between a therapeutic device and a computer or processor according to embodiments of the present invention.

FIG. 14 illustrates an example of a computer interface device 200 that is used to allow communications between a computer 201 (FIGS. 18A, 18B) via a cable 215 extending from a serial (COM) port 215p on the interface device 200 to the compact treatment device 10 via a cable 210. The cable 210 is connected to the interface device 200 at port 212p. The other end 213 of the cable 210 is configured to connect to one or more configurations of the compact therapeutic device 10. The interface device 200 also includes a power input 217. One commercially available programming interface instrument is the AudioPRO from Micro-DSP Technology, LTD, having a serial RS-232C cable that connects to a computer port and a CS44 programming cable that releaseably connects to the treatment device 10. See URL www.micro-dsp.com/product.htm.

Figure 15:
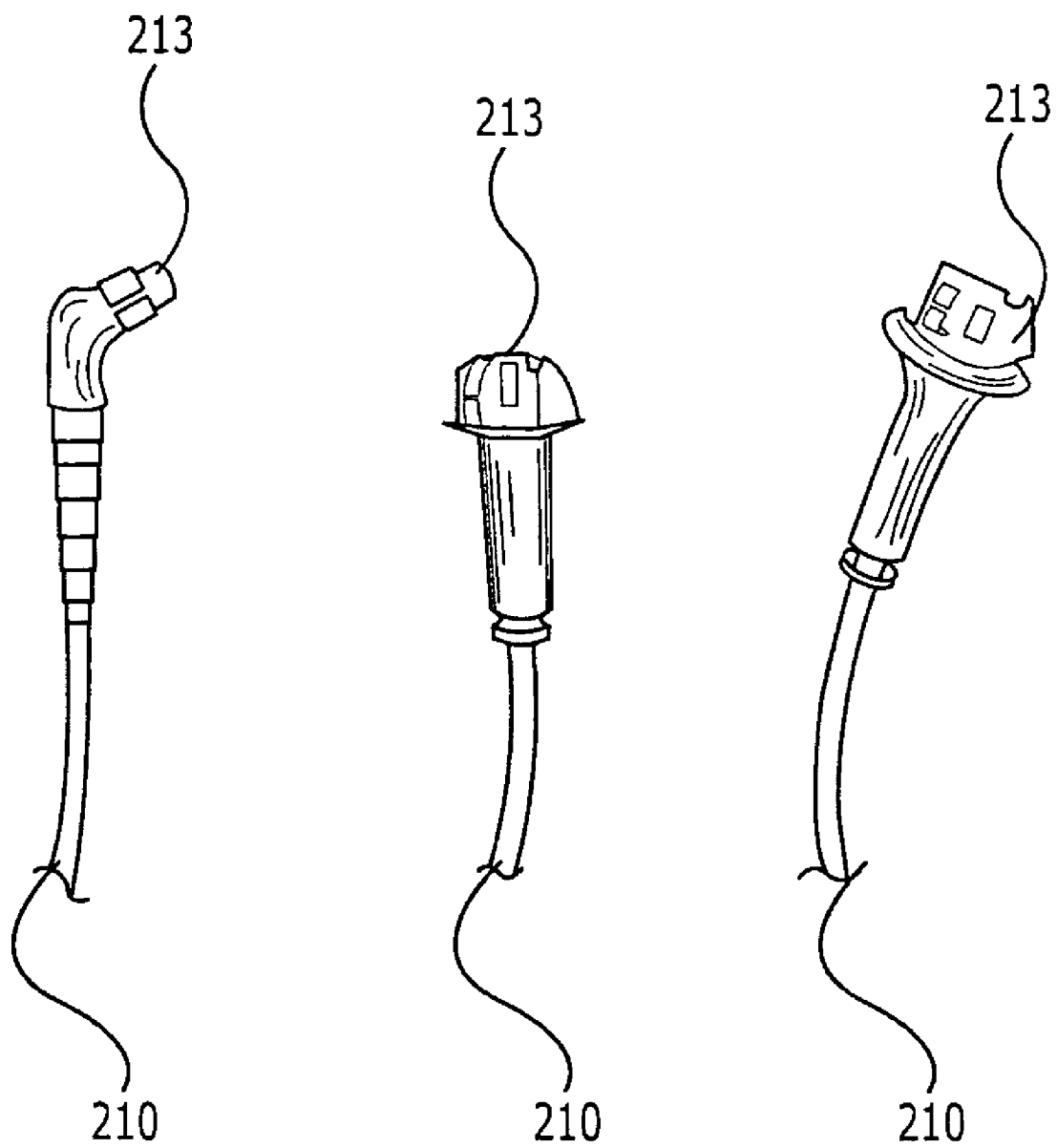
FIG. 15 is an enlarged top view of the treatment device contact end portion of an interface cable configured to connect the device to a programmable interface according to embodiments of the present invention.
Figure 16:
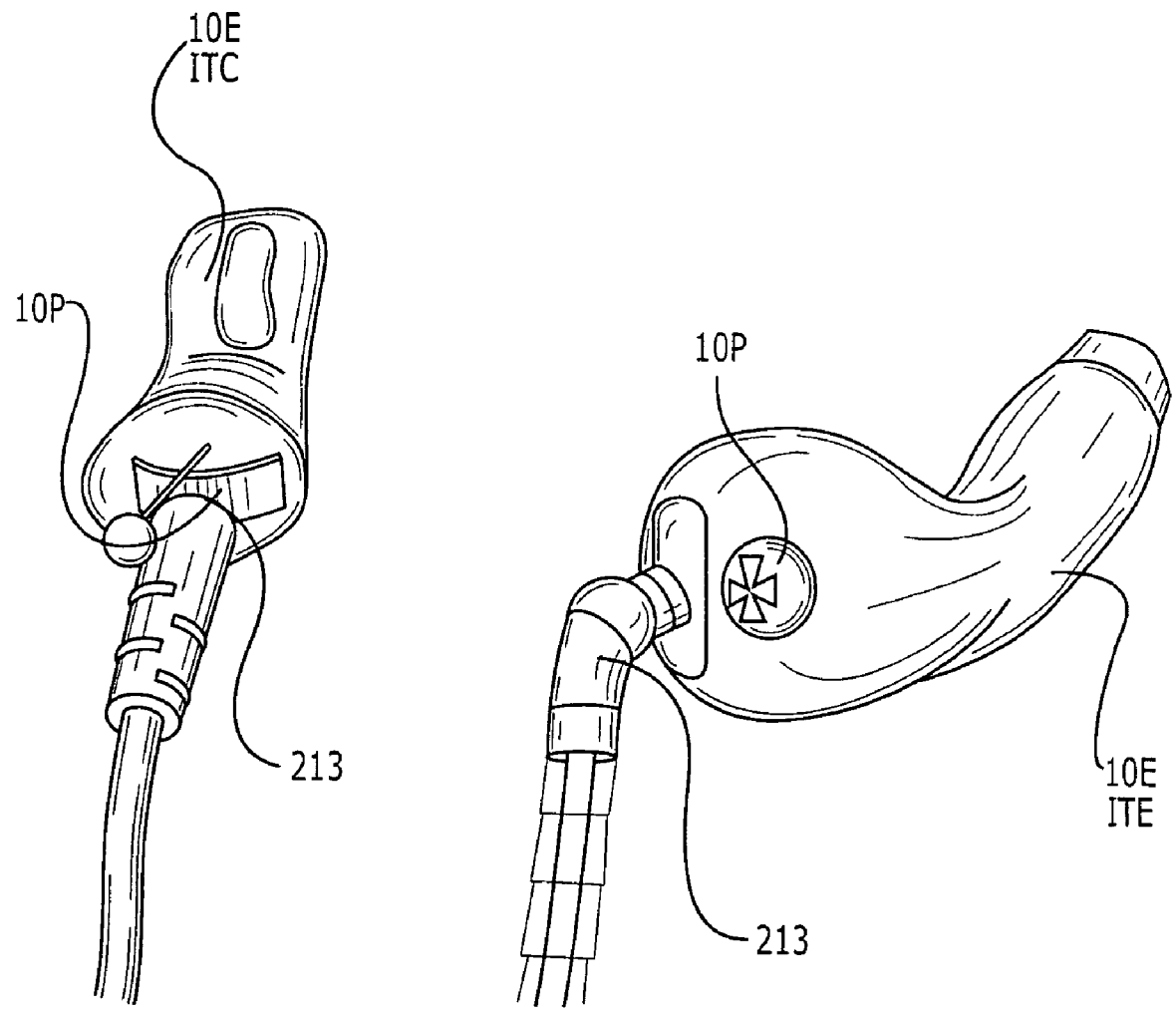
FIG. 16 is an enlarged top view of the interface cable shown in FIGS. 14 and 15 illustrating connection to two exemplary therapeutic devices.
Figure 17:
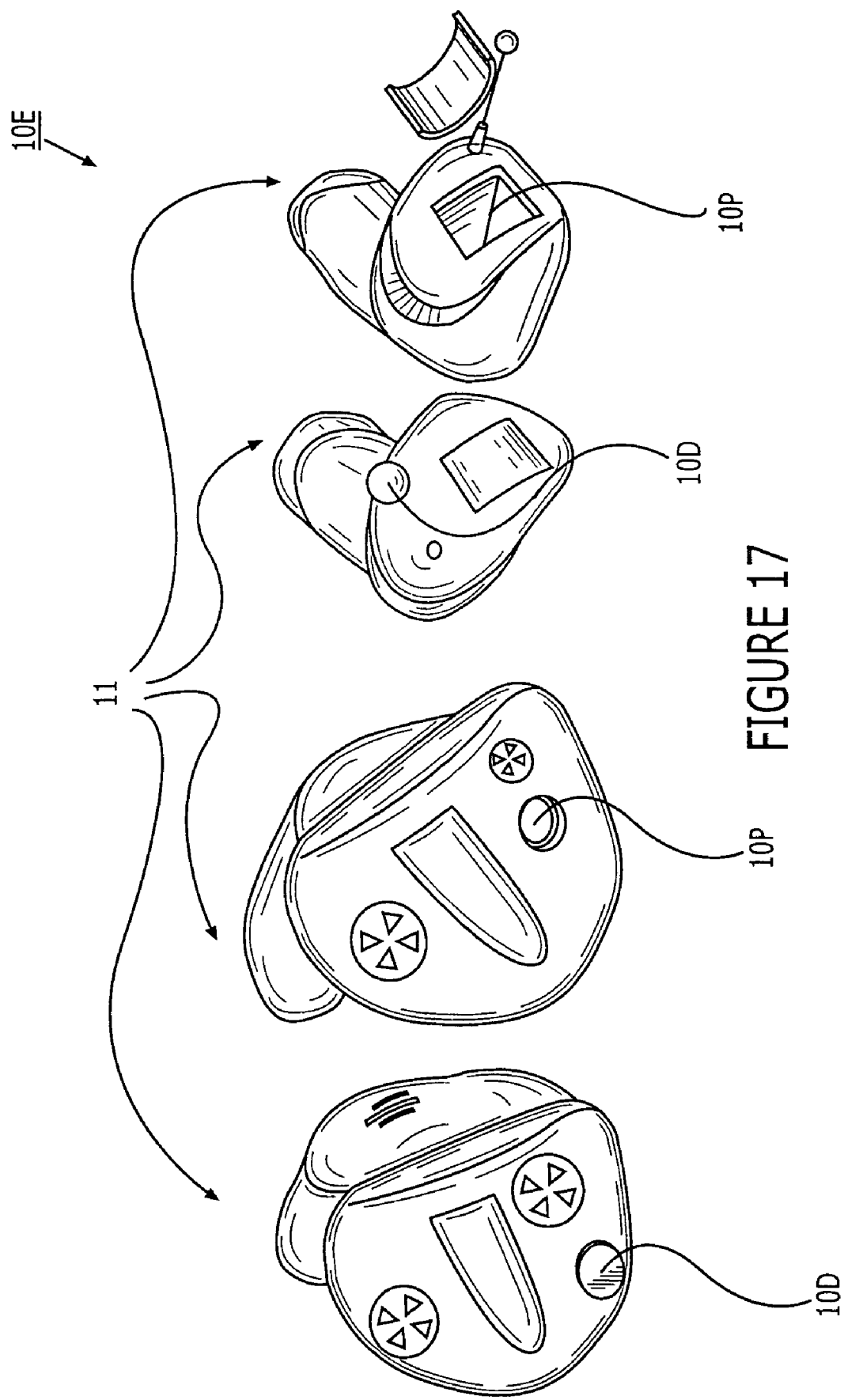
FIG. 17 is a top perspective view of multiple differently sized compact ear mounted devices, each having computer interface access ports according to embodiments of the present invention.

FIG. 15 illustrates an enlarged view of a portion of the cable 210. The end 213 connects directly into a respective compact therapeutic device 10 as shown in FIGS. 16 and 17. FIG. 16 illustrates that an access port 10p, typically accessible by opening an externally releasable door 10D (that may be the battery door) is used to connect the interface cable 210 to the digital signal processor 90. FIG. 17 illustrates two greatly enlarged devices 10E with the cable end connection 213 attached, each of which may have a respective door 10D over the port 10p. The device 10 shown on the left side of FIG. 16 includes or is an ITC device while that shown on the right side includes or is an ITE device. Each has a cable end connection 213 that is modified to connect to the ear-device 10E. As shown, the ITC device connection 213 includes a slender elongated portion to enter into the core of the ITC device.

Figure 18A:
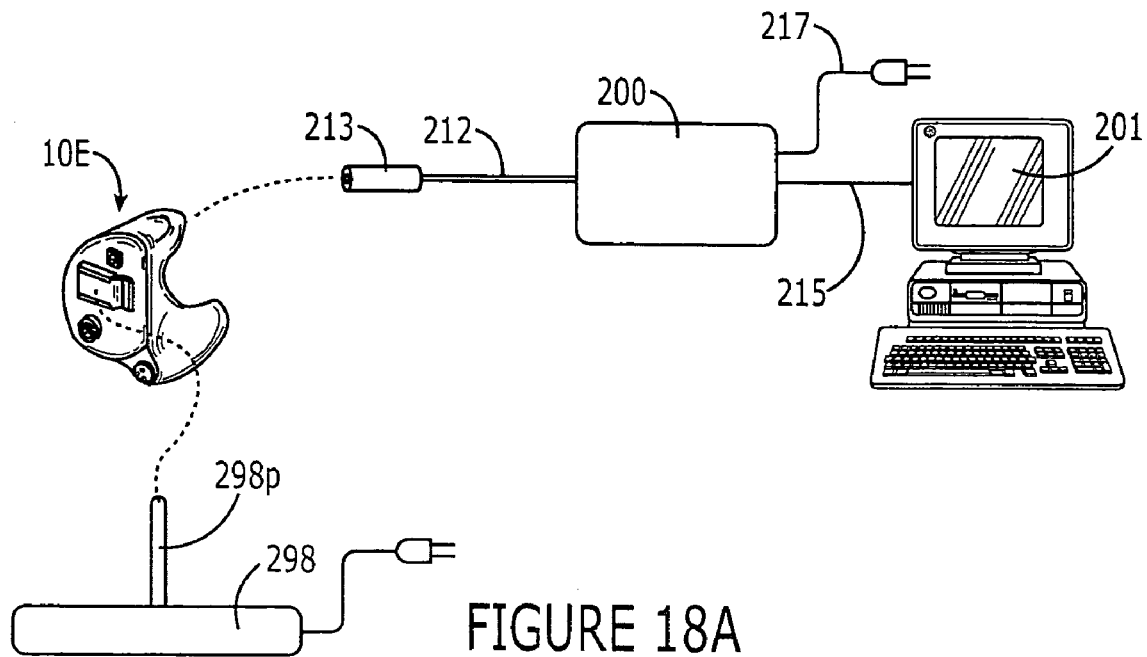
FIG. 18A is a schematic illustration of a single piece, ear mounted treatment device that is configured to communicate with a computer (processor) via an interface cable and that may also be configured to accept a battery charger according to embodiments of the present invention.

FIG. 18A illustrates that the ear-mounted device 10E can serially connect to the programmable interface 200 and a battery charger 298. The battery charger 298 can include a cradle with an upwardly extending prong 298p that extends a distance into the body of the device to communicate with the battery therein. The prong may be configured with a different shape, length or width than that of the data connector 213. Other configurations may be employed as is known to those of skill in the art. In some embodiments, the interface 200 can be configured to also provide a battery charger (not shown).

Figure 18B:
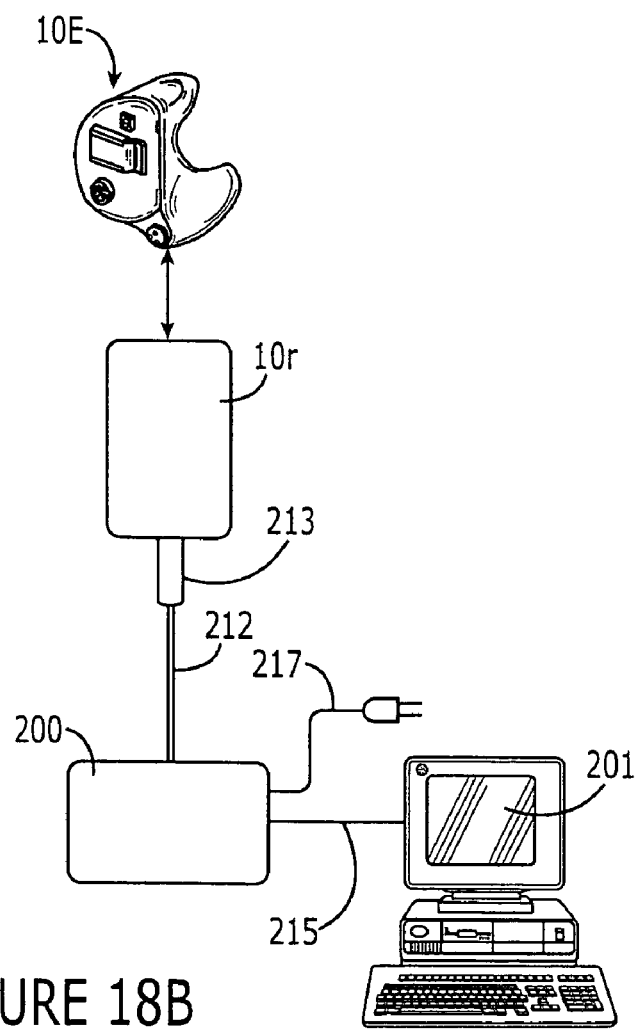
FIG. 18B is a schematic illustration of a two-piece treatment device that communicates with a computer (processor) according to other embodiments of the present invention.

FIG. 18B illustrates that the device 10 includes an ear-mounted device 10E and a wireless second member 10R. The interface 200 can communicate with either or both of the remote 10R and ear mounted member 10E. As shown, the remote member 10R can hold some, or all, of the signal processing circuit 90 while the ear device 10E can hold at least the receiver 70 and speaker/transmitter 24 and a wireless communication circuit. The interface 200 can incorporate the battery charger 298 for the device 10R.

Figure 19:
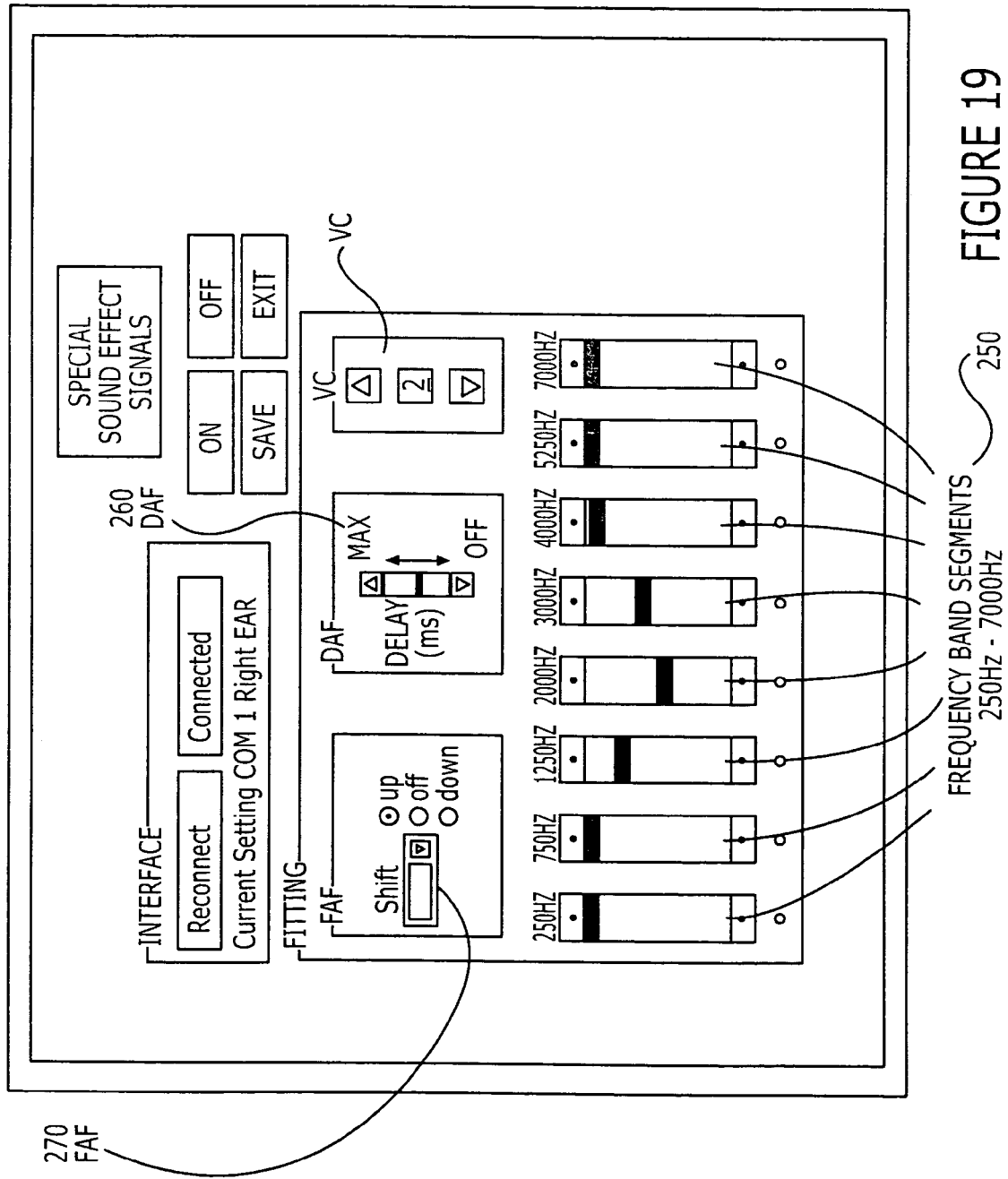
FIG. 19 is a screen view of a programmable input program providing a clinician selectable program parameters according to embodiments of the present invention.

FIG. 19 illustrates a user display input interface used to adjust or select the programmable features of the device 10 to fit or customize to a particular user or condition. The overall gain can be adjusted as well as the gain for each "n" band gain control with associated center frequencies 250 (i.e., where n=eight, each of the eight bands can be respectively centered at a corresponding one of 250 Hz, 750 Hz, 1250 Hz, 2000 Hz, 3000 Hz, 4000 Hz, 5250 Hz, 7000 Hz). Typically, n can be between about 2-20 different bands with spaced apart selected center frequencies. For DAF or other sound effects with delay implementations, the delay can be adjusted by user/programmer or clinician set-up selection 260 in millisecond increments and decrements (to a maximum) and can be turned off as well. The FAF is adjustable via user input 270 by clicking and selecting the frequency desired. The frequency adjustment can be adjustable by desired hertz increments and decrements and may be shifted up, down, and turned off. Octave adjustments may alternately be generated and selectable.

Figure 20:
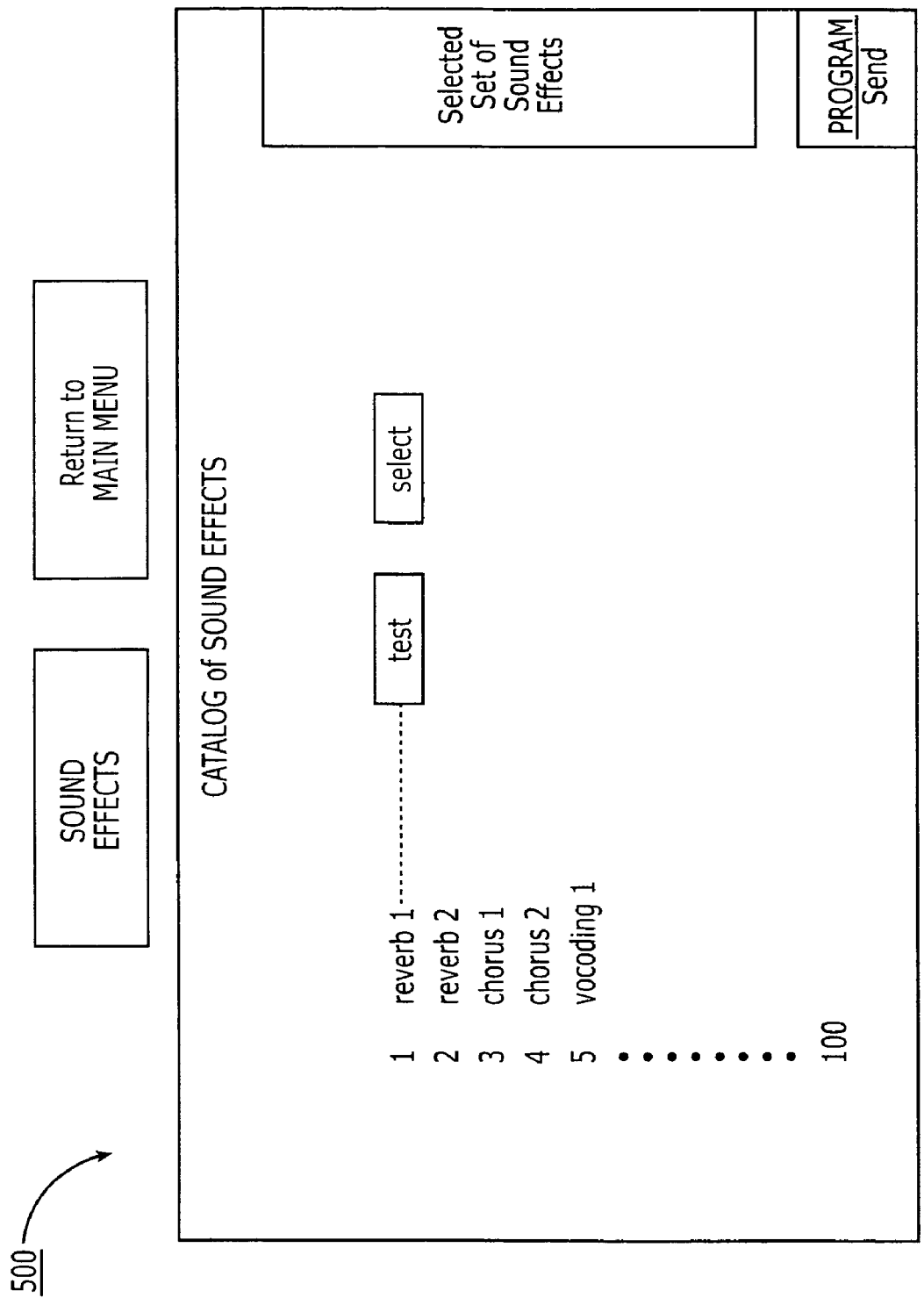
FIG. 20 is a schematic illustration of an example of another input screen that can be used to select sound effect algorithms according to embodiments of the present invention.
Figure 21:
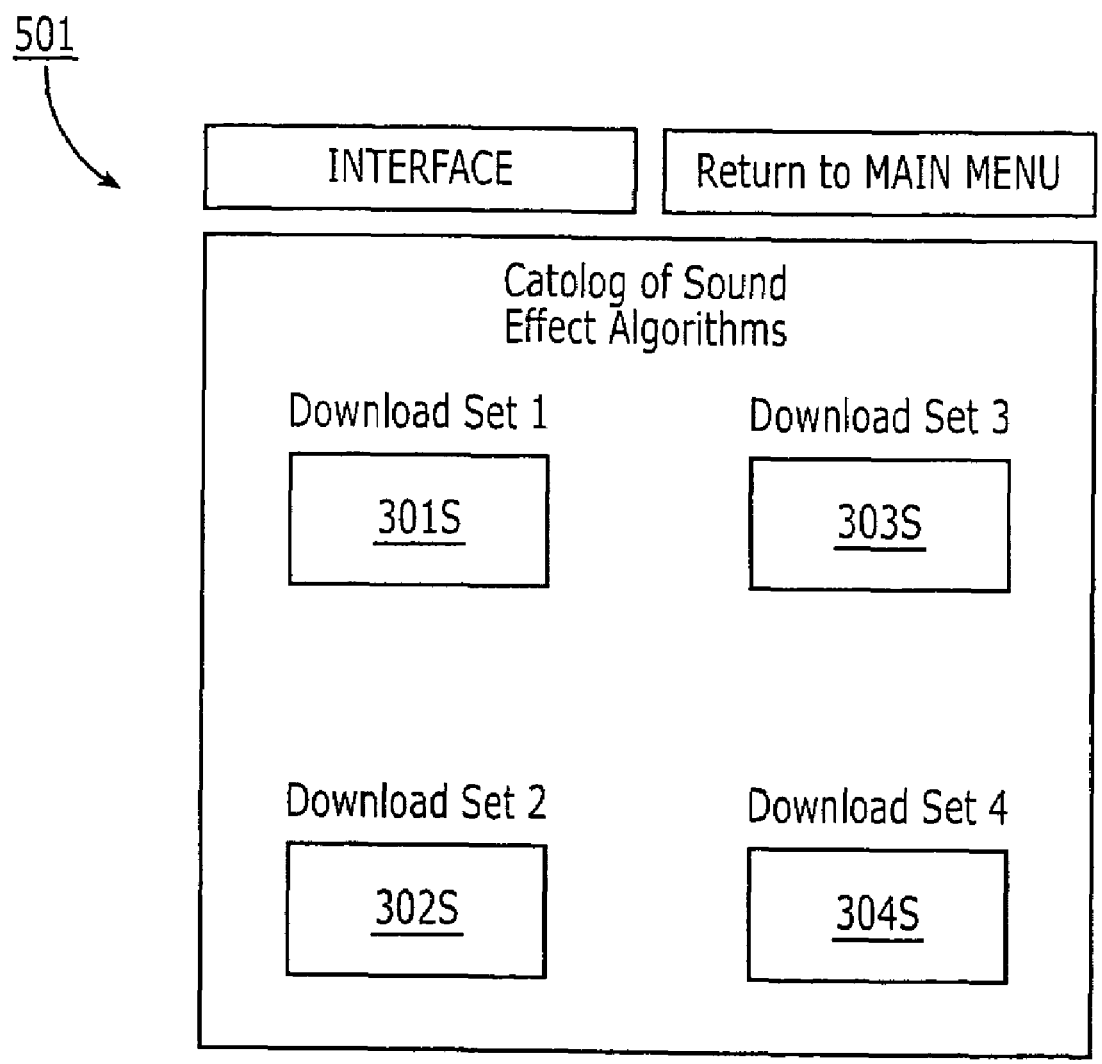
FIG. 21 is a schematic illustration of an example of an input screen according to other embodiments of the present invention.

FIG. 20 is an example of a display interface 500 used to select different sound effects. The display 500 can define a plurality of different sound effects, each or some exemplary ones of which may be selectable for a test evaluation on a user before selection ("test" versus "select"). Each sound effect selected can be put into a set of sound effects that can be sent to memory in the device 10 concurrently. Alternatively, individual ones of the selected sound effects can be sent to the device at the time it is selected as appropriate. In other embodiments, if one or two sound effects are tested, a bundle of sound effects can be automatically selected for use. The bundle can provide a distinct set of varied sounds or related sounds. FIG. 21 illustrates that a user can select one or more predefined sets of sound effects that can be transmitted to the device 10.

As will be appreciated by those of skill in the art, the digital signal processor and other electronic components as described above may be provided by hardware, software, or a combination of the above. Thus, while the various components have been described as discrete elements, they may in practice be implemented by a microprocessor or microcontroller including input and output ports running software code, by custom or hybrid chips, by discrete components or by a combination of the above. For example, one or more of the ADC 76, the delay circuit 78, the voice sample comparator 80, and the gain 86 can be implemented as a programmable digital signal processor device. Of course, the discrete circuit components can also be mounted separately or integrated into a printed circuit board as is known by those of skill in the art. See generally Wayne J. Staab, *Digital Hearing Instruments,* 38 Hearing Instruments No. 11, pp. 18-26 (1987).

In any event, the electroacoustic operating parameters of the device may include individually adjustable and controllable power output, gain, and frequency response components with suitable electroacoustic response. Fixed circuits may also be employed with fixed maximum output, gain, and frequency response while also providing an adjustable volume control for the wearer. In operation, the device in conventional FAF/DAF mode can operate with "low" maximum power output, "mild" gain, and a relatively "wide" and "flat" frequency response. More specifically, in terms of the American National Standards Institute Specification of Hearing Aid Characteristics (ANSI S3.22-1996), the device can have a peak saturated sound pressure level-90 ("SSPL90") equal to or below 110 decibels ("dB") and a high frequency average (HFA) SSPL90 will preferably not exceed 105 dB.

In certain conventional acoustically transparent operating modes, a frequency response can be between at least 200-4000 Hz, and typically between about 200-8000 Hz. In particular conventional mode, the frequency response can be a "flat" in situ response with some compensatory gain between about 1000-4000 Hz. The high frequency average (i.e., 1000, 1600, and 2500) full-on gain is typically between 10-20 dB. For example, the compensatory gain can be about 10-20 dB between 1000-4000 Hz to accommodate for the loss of natural external ear resonance. This natural ear resonance is generally attributable to the occluding in the external auditory meatus and or concha when a CIC, ITE, ITC or ear mold from a BTE device is employed. The total harmonic distortion for an acoustically transparent mode can be less than 10%, and typically less than about 1%. Maximum saturated sound pressure can be about 105 dB SPL with a high frequency average of 95-100 dB SPL and an equivalent input noise that is less than 35 dB, and typically less than 30 dB.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A portable device for treating stuttering or communication disorders, comprising:
   a circuit configured to automatically electronically change sua sponte in a pseudo-random manner one or more parameters used to generate an altered auditory feedback to a user over time;
   a power source in communication with the circuit;
   a receiver in communication with the circuit, the receiver configured to generate an input signal responsive to an auditory signal associated with a user's speech; and
   a speaker in communication with the circuit to output the altered auditory feedback to the user.

2. A portable device according to claim 1, wherein the circuit is configured to electronically sua sponte select different sound effect algorithms used to generate varied altered auditory feedback to a user over time.

3. A portable device according to claim 1, wherein the circuit is configured to automatically electronically change sua sponte at least one of the following parameters used to generate the altered auditory feedback to the user over time:
   a type of sound effect, or electronic filters to automatically electronically generate different altered auditory feedback over time.

4. A portable device according to claim 2, wherein the circuit is configured to intermittently employ the sua sponte selected at least one sound effect algorithm for a short duration to generate a secondary altered auditory feedback signal and primarily output a different altered auditory feedback signal at other times.

5. A portable device according to claim 1, wherein the device comprises an electronic input port configured to electronically receive programmatically selectable sound effect algorithms with adjustable operating parameters and electronic memory configured to store the sound effect algorithms.

6. A portable device according to claim 1, wherein the circuit is configured to activate a selected sound effect having a duty cycle of between about 10-100% and a duration of between about 1 minute to about 7 days.

7. A portable device according to claim 2, wherein the digital signal processor is configured to change the sound effect used to generate the sound effect based altered auditory feedback signal at different time intervals during operation.

8. A portable device according to claim 2, wherein the circuit is configured to change the sound effect used to generate the sound effect based altered auditory feedback signal at constant time intervals.

9. A portable device according to claim 1, wherein the circuit is configured to generate a primary AAF altered auditory feedback signal during operation that is intermittently interrupted with a different altered auditory feedback signal at least about 10 times per week.

10. A portable device according to claim 9, wherein the intermittently generated different altered auditory feedback signal comprises different sound effects used over time during the week, each having a respective duration of less than about 30 minutes.

11. A portable device according to claim 1, wherein the circuit is configured to intermittently change the signal effect used to generate a respective based altered auditory feedback signal at least 3 times per day at different successive time intervals.

12. A portable device according to claim 1, wherein the circuit is configured to change the signal effect used to generate a respective altered auditory feedback signal at least 3 times per day at the same time interval.

13. A portable device according to claim 2, wherein the circuit comprises at least 25 different programmatically selectable sound effects.

14. A portable device according to claim 2, wherein the circuit comprises computer readable storage media with computer program code defining at least 10 different programmatically selectable sound effects, each having predefined audio and/or acoustic sound generating parameters and a respective unique identifier.

15. A portable device according to claim 1, wherein the circuit is configured to change at least signal parameter used to generate a respective altered auditory feedback signal for a short duration at least once during a speaking cycle.

16. A portable device according to claim 1, wherein the circuit is configured to detect the onset of a stuttering event, and wherein the circuit is configured to change a signal parameter used to generate a respective altered auditory feedback signal at least once in response to detection of a stuttering event.

17. A portable device according to claim 2, wherein the circuit is configured to detect the onset of a stuttering event, and wherein the circuit is configured to change the sound effect used to generate a respective altered auditory feedback signal a plurality of times over an eight hour time period relative to detection of a stuttering event and/or an increase in number of stuttering events.

18. A portable device according to claim 17, wherein the circuit is configured to successively change at least twice the sound effect used to generate a respective altered auditory feedback signal proximate in time to detection of a stuttering event.

19. A portable device according to claim 2, wherein the circuit is configured to primarily output a respective altered auditory feedback signal using at least one of a DAF or FAF signal that is interleaved intermittently with at least one sound effect altered auditory feedback signal.

20. A portable device according to claim 1, wherein the circuit is configured to automatically change a selected signal parameter used to generate a respective signal effect altered auditory signal substantially continuously over use, and wherein at least some of the changed signal effects selected have a duration that is less than about 10 minutes.

21. A portable device according to claim 2, wherein a plurality of the sound effect algorithms are configured to generate reverberation sound effects.

22. A portable device according to claim 2, wherein some of the sound effect algorithms are configured to generate chorus and flanging sound effects.

23. A portable device according to claim 1, wherein the device is self-contained and holds the circuit, the receiver, the power source and the speaker and is configured to be supported by the ear of a user, the housing having opposing distal and proximal surfaces, wherein at least said proximal surface is configured for positioning in the ear canal of a user.

24. A portable device according to claim 1, wherein the device comprises a first member with at least the receiver and speaker configured to be supported by the ear or head of a user and a remote second member configured to communicate with the first member.

25. A portable device according to claim 24, wherein the second member is configured to wirelessly communicate with the first member.

26. A portable device according to claim 1, wherein the device is configured to treat stuttering.

27. A portable device according to claim 1, wherein the circuit is configured to electronically sua sponte pseudo-randomly alter at least one signal parameter used to generate the altered auditory feedback at least daily.

28. A portable device according to claim 1, wherein the altered auditory feedback includes sound effect feedback that are multi-parameter adjustments not just adjustment to a frequency for FAF or a delay for DAF.

29. A portable device according to claim 1, wherein the circuit comprises a plurality of predefined sound effects, and wherein each sound effect has multiple associated audio and acoustic parameters, including at least two of the following: a low pass filter, a decay time(s), a delay, a frequency range, amplitude and an animation velocity used to generate the sound effect.

30. A portable device according to claim 1, wherein the circuit is configured to generate a reverberation sound effect to generate the altered auditory feedback.

31. A portable device according to claim 29, wherein the sound effects each have an alphanumeric serial identifier or are related to a spatial location on an electronic storage media in the device having an alphanumeric identifier, and wherein the circuit is configured to select the sound effect serially based on their alphanumeric identifier.

32. A portable device comprising:
   a circuit configured to automatically electronically change sua sponte in a pseudo-random manner one or more parameters used to generate an altered auditory feedback to a user over time, wherein the circuit is configured to electronically sua sponte select different sound effect algorithms used to generate varied altered auditory feedback to a user over time,
   wherein the circuit is in communication with a power source and comprises:
   a digital signal processor;
   a receiver in communication with the digital signal processor, said receiver configured to generate an input signal responsive to an auditory signal associated with a user's speech;
   an altered auditory feedback circuit including a sound effect selector module for selecting one of a plurality of pre-defined different sound effect algorithms including non-delay based sound effects operably associated with the receiver and the digital signal processor for generating and transmitting the altered auditory signal to the user; and
   a speaker in communication with the altered auditory feedback circuit, the speaker adapted to reside in or proximate the ear of the user.

33. A method for treating stuttering or communication disorders, comprising:
   receiving a speech signal from a user;
   selecting, sua sponte, at least one of a plurality of programmatically selectable signal effects used to generate an altered auditory feedback; then
   digitally generating an altered auditory feedback signal using the received speech signal and the at least one sua sponte selected signal effect to thereby provide an adaptation-resistant altered feedback signal to the subject.

34. A method according to claim 33, wherein the sua sponte selecting the programmatically selectable signal effect comprises selecting at least one of a plurality of programmatically selectable sound effects, each having a plurality of associated signal parameters, and wherein the digitally generating comprises digitally generating the altered auditory feedback signal using the received speech signal and the at least one sua sponte selected sound effect to thereby provide an adaptation-resistant altered feedback signal to the subject.

35. A method according to claim 34, wherein the programmatically selectable sound effects have a serial identifier, and wherein the selecting is carried out by serially selecting the programmatically selectable sound effects.

36. A method according to claim 34, further comprising:
electronically storing in a portable device, a first set of sound effect algorithms having associated predefined audio and acoustic digital signal parameters at a first point in time; and
subsequently electronically storing in the portable device, a second set of sound effect of sound effect algorithms having associated predefined audio and acoustic digital signal parameters.

37. A method according to claim 36, wherein the second set replaces the first set.

38. A method according to claim 36, wherein the second set supplements the first set.

39. A method according to claim 33, wherein the user has a diagnosed learning disability ("LD").

40. A method according to claim 33, wherein the user has a stuttering impediment.

41. A method according to claim 34, further comprising electronically storing a plurality of predefined sound effect algorithms in a portable device, the sound effect algorithms comprising reverberation and echo sound effects.

42. A method according to claim 41, wherein the predefined sound effect algorithms have at least one different associated audio and acoustic parameter and each has a unique identifier.

43. A method according to claim 33, wherein the sua sponte selection changes the signal effect used to generate the altered auditory feedback signal at different successive time intervals.

44. A method according to claim 34, wherein the sua sponte selection changes the sound effect used to generate the altered auditory feedback signal at least 20 times per week.

45. A method according to claim 34, wherein the sua sponte selection changes the sound effect used to generate the altered auditory feedback signal at least 3 times per day at different successive time intervals.

46. A method according to claim 34, wherein the sua sponte selection changes the sound effect used to generate the altered auditory feedback signal at least 3 times per day at the same time interval.

47. A method according to claim 34, wherein the sua sponte selection is carried out by selecting at least one of at least 100 different programmatically selectable sound effects.

48. A method according to claim 34, wherein the sua sponte selection is carried out by selecting at least one of at least 10 different programmatically selectable sound effects, each having predefined audio and/or acoustic sound generating parameters and a respective unique identifier.

49. A method according to claim 34, wherein the sua sponte selection changes the sound effect used to generate the altered auditory feedback signal at least once during a speaking cycle.

50. A method according to claim 33, further comprising detecting an onset of a stuttering event, and wherein the sua sponte selection changes the signal effect used to generate the altered auditory feedback signal at least once in response to detection of a stuttering event.

51. A method according to claim 34, wherein the sua sponte selection changes the sound effect used to generate the altered auditory feedback signal a plurality of times over an eight hour time period relative to detection of a stuttering event and/or an increase in number of stuttering events.

52. A method according to claim 34, further comprising electronically detecting a stuttering event or an increase in number of stuttering events, wherein the sua sponte selection successively changes the sound effect used to generate the altered auditory feedback signal proximate in time to detection of a stuttering event or an increase in number of stuttering events.

53. A computer program product for generating an adaptation resistant altered auditory feedback signal to a patient, the computer program product comprising:
a computer readable storage medium having computer readable program code embodied in the medium, the computer-readable program code comprising:
computer readable program code configured to define a plurality of different sound effects, each associated with a unique identifier;
computer readable program code configured to automatically select at least one of the plurality of different sound effects for use in generating an altered auditory feedback signal intermittently for a short duration; and
computer readable program code configured to generate an altered auditory feedback signal using a speech signal from the patient and the selected at least one sound effect to thereby provide an adaptation resistant altered feedback signal to the patient.

54. A computer program product according to claim 53, wherein the computer program code configured to select the sound effect comprises computer program code configured to define a pseudo-random sound effect selector.

55. A computer program product according to claim 53, wherein the computer program code configured to select the sound effect comprises computer program code configured to define a random number generator used to select the sound effect using the sound effect identifier.

56. A computer program product according to claim 53, wherein each sound effect has multiple associated audio and acoustic parameters, including at least two of the following: a low pass filter, a decay time(s), a delay, a frequency range, amplitude and an animation velocity used to generate the sound effect.

57. A computer program product according to claim 53, wherein the computer readable program code that defines the different sound effects comprises at least a plurality of reverberation sound effects.

58. A computer program product according to claim 53, wherein the sound effects each have an alphanumeric serial identifier or are related to a spatial location on an electronic storage media having an alphanumeric identifier, and wherein the computer program code configured to select the sound effect comprises computer program code configured to serially select the sound effects based on their alphanumeric identifier.

59. A computer program product according to claim 53, further comprising computer readable program code configured to output certain sound effects in stereo to two discrete ear supported housings, one for each ear, used to deliver the altered auditory feedback signal to the user in stereo.

60. A computer program product according to claim 53, wherein the computer readable program code configured to automatically select at least one of the plurality of different sound effects for use in generating an altered auditory feedback signal at different times is configured to change the selected at least one sound effect at irregular time intervals.

61. A computer program product according to claim 53, wherein the computer readable program code configured to automatically select at least one of the plurality of different sound effects for use in generating an altered auditory feedback signal at different times is configured to change the selected at least one sound effect at different successive time intervals and for different time durations.

62. A computer program product according to claim 53, wherein the computer readable program code configured to automatically select at least one of the plurality of different sound effects for use in generating an altered auditory feedback signal at different times is configured to change the selected at least one sound effect at the same successive time interval.

63. A computer program product according to claim 53, wherein the computer readable program code configured to automatically select at least one of the plurality of different sound effects for use in generating an altered auditory feedback signal at different times is configured to change the at least one sound effect used to generate the altered auditory feedback signal at different successive time intervals ranging from every minute to at least twice weekly.

64. A computer program product according to claim 53, wherein the computer readable program code configured to automatically select at least one of the plurality of different sound effects for use in generating an altered auditory feedback signal at different times is configured to change the selected at least one sound effect used to generate the altered auditory feedback signal at least 20 times per week.

65. A computer program product according to claim 53, wherein the computer readable program code configured to automatically select at least one of the plurality of different sound effects for use in generating an altered auditory feedback signal at different time is configured to change the at least one sound effect used to generate the altered auditory feedback signal at least 3 times per day at different successive time intervals.

66. A computer program product according to claim 53, wherein the computer readable program code configured to automatically select at least one of the plurality of different sound effects for use in generating an altered auditory feedback signal at different times is configured to change the at least one sound effect used to generate the altered auditory feedback signal at least 3 times per day at the same time interval.

67. A computer program product according to claim 53, wherein the computer readable program code configured to define a plurality of different sound effects, each having a unique identifier comprises at least 1000 different programmatically selectable sound effects.

68. A computer program product according to claim 53, wherein the computer readable program code configured to automatically select at least one of the plurality of different sound effects for use in generating an altered auditory feedback signal at different times is configured to change the at least one sound effect used to generate the altered auditory feedback signal at least 20 times per week.

69. A computer program product for generating different automatically changed adaptation resistant altered auditory feedback to a patient, the computer program product comprising:
a computer readable storage medium having computer readable program code embodied in the medium, the computer-readable program code comprising:
computer readable program code configured to automatically change at least one signal parameter in a pseudo-random manner to generate different altered auditory feedback to a user over time to thereby provide adaptation resistant feedback to the user.

70. A computer program product according to claim 69, further comprising computer readable program code configured to select an activation and deactivation time of the selected altered auditory feedback, a duration, and a duty cycle of the selected auditory feedback.

71. A portable device for treating stuttering, comprising:
a portable housing;
a circuit in the housing configured to automatically electronically output a DAF or FAF signal to a user and sua sponte automatically electronically provide a sound effect having a set of operational parameters different from the DAF or FAF signal that is perceptually significant to a user as an altered auditory feedback signal before or after the DAF or FAF signal to generate adaptation resistant altered auditory feedback to a user over time;
a power source in the housing in communication with the circuit;
a receiver in communication with the circuit, the receiver configured to generate an input signal responsive to an auditory signal associated with a user's speech; and
a speaker in communication with the circuit to output the altered auditory feedback to the user.

72. A portable device according to claim 71, wherein the sound effect is configured to be more disruptive to speech of the user than the DAF or FAF signal.

73. A device for treating stuttering comprising:
a circuit configured to electronically sua sponte select different sound effects from an electronic library of pre-defined sound effects to generate varied altered auditory feedback to a user over time to treat stuttering;
a power source in communication with the circuit;
a receiver in communication with the circuit, the receiver configured to generate an input signal responsive to an auditory signal associated with a user's speech; and
a speaker in communication with the circuit to output the altered auditory feedback to the user.

* * * * *

UNITED STATES PATENT AND TRADEMARK OFFICE
CERTIFICATE OF CORRECTION

PATENT NO. : 7,591,779 B2 Page 1 of 1
APPLICATION NO. : 11/213581
DATED : September 22, 2009
INVENTOR(S) : Kalinowski et al.

It is certified that error appears in the above-identified patent and that said Letters Patent is hereby corrected as shown below:

Col. 30, Claim 33, Line 63: Please correct "*sua sponte*, at least" to read -- *sua sponte* in a pseudo-random manner, at least --.

Signed and Sealed this

Fifth Day of January, 2010

David J. Kappos
*Director of the United States Patent and Trademark Office*